United States Patent
Kim et al.

(10) Patent No.: US 11,542,530 B2
(45) Date of Patent: Jan. 3, 2023

(54) METHOD FOR INCREASING EFFICIENCY OF HOMOLOGOUS RECOMBINATION-BASED GENE EDITING IN PLANT

(71) Applicant: INDUSTRY-ACADEMIC COOPERATION FOUNDATION GYEONGSANG NATIONAL UNIVERSITY, Gyeongsangnam-do (KR)

(72) Inventors: Jae Yean Kim, Gyeongsangnam-do (KR); Tien Van Vu, Gyeongsangnam-do (KR); Velu Sivankalyani, Gyeongsangnam-do (KR); Mil Thi Tran, Gyeongsangnam-do (KR); Jihae Kim, Gyeongsangnam-do (KR); Yeon Woo Sung, Gyeongsangnam-do (KR); Se Jeong Jeong, Gyeongsangnam-do (KR); Hyun Jeong Kim, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 156 days.

(21) Appl. No.: 16/963,965

(22) PCT Filed: Jan. 11, 2019

(86) PCT No.: PCT/KR2019/000501
§ 371 (c)(1),
(2) Date: Jul. 22, 2020

(87) PCT Pub. No.: WO2019/143077
PCT Pub. Date: Jul. 25, 2019

(65) Prior Publication Data
US 2021/0040505 A1 Feb. 11, 2021

(30) Foreign Application Priority Data
Jan. 22, 2018 (KR) .................... 10-2018-0007579

(51) Int. Cl.
| | |
|---|---|
| C12N 15/82 | (2006.01) |
| C12N 15/90 | (2006.01) |
| C12N 9/22 | (2006.01) |
| C12N 15/113 | (2010.01) |

(52) U.S. Cl.
CPC ............ *C12N 15/902* (2013.01); *C12N 9/22* (2013.01); *C12N 15/113* (2013.01); *C12N 2310/20* (2017.05)

(58) Field of Classification Search
CPC .................... C12N 2310/20; C12N 15/902
See application file for complete search history.

(56) References Cited

FOREIGN PATENT DOCUMENTS

| | | |
|---|---|---|
| JP | 2010-187597 A | 9/2010 |
| JP | 2018-000129 A | 1/2018 |
| KR | 10-2017-0081268 A | 7/2017 |
| WO | WO 2016/164356 A1 | 10/2016 |
| WO | WO 2017/066175 A1 | 4/2017 |

OTHER PUBLICATIONS

LeBlanc, Chantal, et al. "Increased efficiency of targeted mutagenesis by CRISPR/Cas9 in plants using heat stress." The Plant Journal 93.2 (2018): 377-386. (Year: 2018).*
Maruyama T, Dougan SK, Truttmann MC, Bilate AM, Ingram JR, Ploegh HL (2015) Increasing the efficiency of precise genome editing with CRISPR-Cas9 by inhibition of nonhomologous end joining. Nature Biotechnology 33: 538-542 (Year: 2015).*
Wang, Mugui, et al. "Gene targeting by homology-directed repair in rice using a geminivirus-based CRISPR/Cas9 system." Molecular plant 10.7 (2017): 1007-1010. (Year: 2017).*
Chen, Qiang, et al. "Geminiviral vectors based on bean yellow dwarf virus for production of vaccine antigens and monoclonal antibodies in plants." Human vaccines 7.3 (2011): 331-338. (Year: 2011).*
Sun, Yongwei, et al. "Engineering herbicide-resistant rice plants through CRISPR/Cas9-mediated homologous recombination of acetolactate synthase." Molecular plant 9.4 (2016): 628-631. (Year: 2016).*
LeBlanc, Chantal, et al. "Increased efficiency of targeted mutagenesis by CRISPR/Cas9 in plants using heat stress." The Plant Journal 93.2 (2018): 377-386. (Year: 2017).*
Song, Jun, et al. "RS-1 enhances CRISPR/Cas9-and TALEN-mediated knock-in efficiency." Nature communications 7.1 (2016): 1-7 . (Year: 2016).*
Vartak, Supriya V., and Sathees C. Raghavan. "Inhibition of non-homologous end joining to increase the specificity of CRISPR/Cas9 genome editing." The FEBS journal 282.22 (2015): 4289-4294. (Year: 2015).*
International Search Report for PCT/KR2019/000501 dated Apr. 12, 2019.
NCBI, GenBank accession No. CP002688.1 "*Arabidopsis thaliana* chromosome 5 sequence" (Jul. 20, 2017). See the entire document.
Nicholas J. Baltes et al., "DNA Replicons for Plant Genome Engineering", The Plant Cell, vol. 26:151-163, Jan. 2014.

(Continued)

*Primary Examiner* — Weihua Fan
(74) *Attorney, Agent, or Firm* — The PL Law Group, PLLC

(57) ABSTRACT

A method for increasing the efficiency of homologous recombination-based gene editing in a plant according to an embodiment of the present invention includes optimizing temperature and photoperiod conditions during tissue culture of plant cells, expressing factors required for homology-directed DNA repair (HDR) and factors for increasing the HDR efficiency by using a multiple replicon, or regulating the HDR pathway or non-homologous end joining (NHEJ) pathway.

6 Claims, 17 Drawing Sheets

Specification includes a Sequence Listing.

(56) References Cited

OTHER PUBLICATIONS

Tomas Cermak et al., "High-frequency, precise modification of the tomato genome", Genome Biology, 2015.
Wang et al. "Gene Targeting by Homology-Directed Repair in Rice Using a Geminivirus-Based CRISPR/Cas9 System", Mol Plant. 10(7):1007-1010, 2017.
LeBlanc et al., "Increased efficiency of targeted mutagenesis by CRISPR/Cas9 in plants using heat stress" Plant J. 93 (2):377-386, 2018.
Nishizawa-Yokoi et al., "A Defect in DNA Ligase4 Enhances the Frequency of TALEN-Mediated Targeted Mutagenesis in Rice", Plant Physiol. 170(2):653-666, 2016.
Rongxue Peng et al., "Potential pitfalls of CRISPR/Cas9-mediated genome editing", FEBS Journal. vol. 283, p. 1218-1231, 2016.

\* cited by examiner

FIG. 3

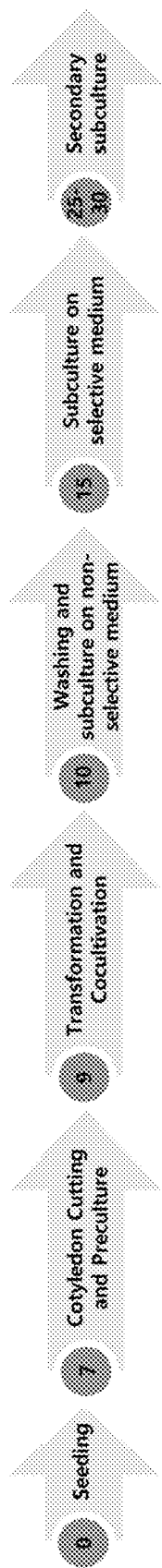

Explant treatment:
- Seed germination; 25°C, 3-4 days at dark conditions and 3-4 days at light conditions
- Preculture; 25°C, 1 day at dark conditions
- Cocultivation; 25°C, 2 days at dark conditions
- Washing; 2 times with 500 mg/L timentin or cefotaxime, drying using sterile Whatman paper
- After washing; cultivation at 25-31°C, light/dark conditions
- Cultivation on non-selective medium; 5 days
- Subsequent subculture; carried out with an interval of 10 to 12 days FIG. 4
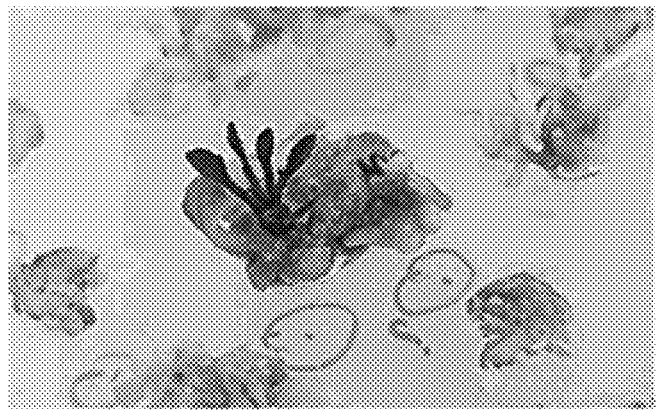
HDR-edited tomato stem regenerated after transformation, HR ex 6-light
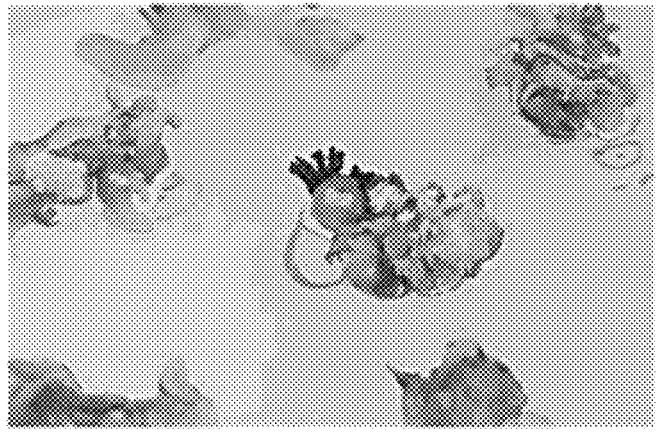
HDR-edited tomato stem regenerated after transformation, HR ex 6-dark

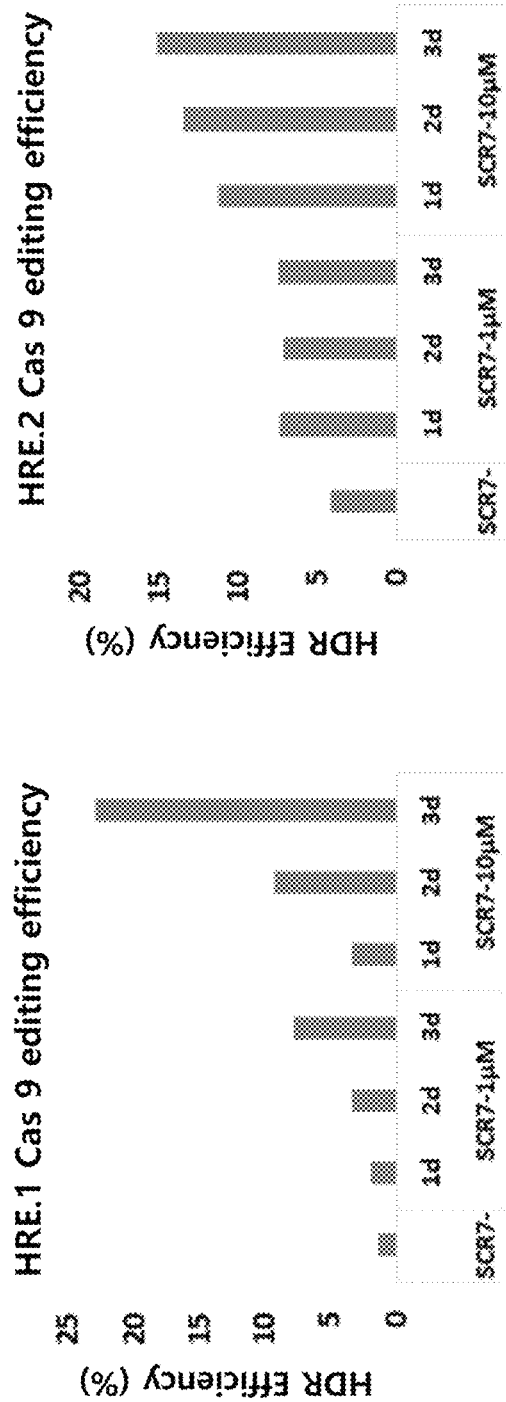
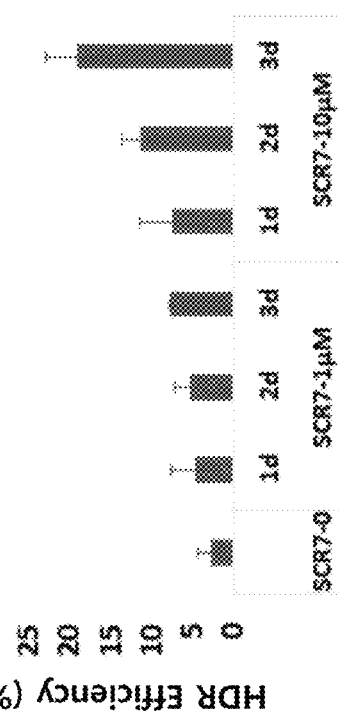
FIG. 10

SEQUENCE LISTING

```
<160> NUMBER OF SEQ ID NOS: 31

<210> SEQ ID NO 1
<211> LENGTH: 110
<212> TYPE: DNA
<213> ORGANISM: Arabidopsis thaliana

<400> SEQUENCE: 1
gtaaagcctc gattttggg tttaggtgtc tgcttattag agtaaaaaca catcctttga      60
aattgtttgt ggtcatttga ttgtgctctt gatccattga attgctgcag              110

<210> SEQ ID NO 2
<211> LENGTH: 304
<212> TYPE: DNA
<213> ORGANISM: Arabidopsis thaliana

<400> SEQUENCE: 2
gtaaatttct gtgttcctta ttctctcaaa atcttcgatt ttgttttcgt tcgatcccaa     60
tttcgtatat gttctttggt ttagattctg ttaatcttag atcgaagatg attttctggg   120
tttgatcgtt agatatcatc ttaattctcg attagggttt catagatatc atccgatttg   180
ttcaaataat ttgagttttg tcgaataatt actcttcgat ttgtgatttc tatctagatc   240
tggtgttagt ttctagtttg tgcgatcgaa tttgtcgatt aatctgagtt tttctgatta   300
acag                                                                304

<210> SEQ ID NO 3
<211> LENGTH: 13
<212> TYPE: DNA
<213> ORGANISM: Artificial Sequence
<220> FEATURE:
<223> OTHER INFORMATION: Kozak sequence

<400> SEQUENCE: 3
agactcaatg atg                                                       13

<210> SEQ ID NO 4
<211> LENGTH: 20
<212> TYPE: DNA
<213> ORGANISM: Artificial Sequence
<220> FEATURE:
```

<223> OTHER INFORMATION: gRNA

<400> SEQUENCE: 4
atcaagttaa cgtttatctt                                                    20

<210> SEQ ID NO 5
<211> LENGTH: 20
<212> TYPE: DNA
<213> ORGANISM: Artificial Sequence
<220> FEATURE:
<223> OTHER INFORMATION: gRNA

<400> SEQUENCE: 5
attagagatt ataaatttaa                                                    20

<210> SEQ ID NO 6
<211> LENGTH: 20
<212> TYPE: DNA
<213> ORGANISM: Artificial Sequence
<220> FEATURE:
<223> OTHER INFORMATION: gRNA

<400> SEQUENCE: 6
tttacaataa tatatagtaa                                                    20

<210> SEQ ID NO 7
<211> LENGTH: 20
<212> TYPE: DNA
<213> ORGANISM: Artificial Sequence
<220> FEATURE:
<223> OTHER INFORMATION: gRNA

<400> SEQUENCE: 7
aagttgttag ctagagtttc                                                    20

<210> SEQ ID NO 8
<211> LENGTH: 20
<212> TYPE: DNA
<213> ORGANISM: Artificial Sequence
<220> FEATURE:
<223> OTHER INFORMATION: gRNA

<400> SEQUENCE: 8
ttttaaaaga aaaaattaaa                                                    20

<210> SEQ ID NO 9
<211> LENGTH: 20
<212> TYPE: DNA
<213> ORGANISM: Artificial Sequence
<220> FEATURE:
<223> OTHER INFORMATION: gRNA

<400> SEQUENCE: 9
atacatattt atgtttgtta                                                    20

<210> SEQ ID NO 10
<211> LENGTH: 20
<212> TYPE: DNA
<213> ORGANISM: Artificial Sequence
<220> FEATURE:
<223> OTHER INFORMATION: gRNA

<400> SEQUENCE: 10
tgcccaacta acgctcaaaa                                                    20

```
<210> SEQ ID NO 11
<211> LENGTH: 20
<212> TYPE: DNA
<213> ORGANISM: Artificial Sequence
<220> FEATURE:
<223> OTHER INFORMATION: gRNA

<400> SEQUENCE: 11
tgataataac aaaaatgacg                                                   20

<210> SEQ ID NO 12
<211> LENGTH: 20
<212> TYPE: DNA
<213> ORGANISM: Artificial Sequence
<220> FEATURE:
<223> OTHER INFORMATION: gRNA

<400> SEQUENCE: 12
aaaaaaattt gtatgttgtt                                                   20

<210> SEQ ID NO 13
<211> LENGTH: 20
<212> TYPE: DNA
<213> ORGANISM: Artificial Sequence
<220> FEATURE:
<223> OTHER INFORMATION: gRNA

<400> SEQUENCE: 13
tattatttta tgttattgtt                                                   20

<210> SEQ ID NO 14
<211> LENGTH: 20
<212> TYPE: DNA
<213> ORGANISM: Artificial Sequence
<220> FEATURE:
<223> OTHER INFORMATION: gRNA

<400> SEQUENCE: 14
tagcatatga ccaaaataaa                                                   20

<210> SEQ ID NO 15
<211> LENGTH: 20
<212> TYPE: DNA
<213> ORGANISM: Artificial Sequence
<220> FEATURE:
<223> OTHER INFORMATION: gRNA

<400> SEQUENCE: 15
taacaaaaca gaaaaagaag                                                   20

<210> SEQ ID NO 16
<211> LENGTH: 20
<212> TYPE: DNA
<213> ORGANISM: Artificial Sequence
<220> FEATURE:
<223> OTHER INFORMATION: gRNA

<400> SEQUENCE: 16
atgtgaccca atactttaag                                                   20

<210> SEQ ID NO 17
<211> LENGTH: 20
<212> TYPE: DNA
<213> ORGANISM: Artificial Sequence
<220> FEATURE:
<223> OTHER INFORMATION: gRNA
```

```
<400> SEQUENCE: 17
tataccctta aactatattc                                                 20

<210> SEQ ID NO 18
<211> LENGTH: 20
<212> TYPE: DNA
<213> ORGANISM: Artificial Sequence
<220> FEATURE:
<223> OTHER INFORMATION: gRNA

<400> SEQUENCE: 18
ttctatgcat aaataattaa                                                 20

<210> SEQ ID NO 19
<211> LENGTH: 20
<212> TYPE: DNA
<213> ORGANISM: Artificial Sequence
<220> FEATURE:
<223> OTHER INFORMATION: gRNA

<400> SEQUENCE: 19
gagagaaaga agcctcctca                                                 20

<210> SEQ ID NO 20
<211> LENGTH: 20
<212> TYPE: DNA
<213> ORGANISM: Artificial Sequence
<220> FEATURE:
<223> OTHER INFORMATION: gRNA

<400> SEQUENCE: 20
agctctaaat gataaagttg                                                 20

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
ttgagatgag cacttgggat ag                                              22

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
cgtaagcctc tctaaccatc tg                                              22

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
gttctgtcag ttccaaacgt aaa                                             23

<210> SEQ ID NO 24
<211> LENGTH: 20
```

```
<212> TYPE: DNA
<213> ORGANISM: Artificial Sequence
<220> FEATURE:
<223> OTHER INFORMATION: primer

<400> SEQUENCE: 24
atctcgcggt acatccaatc                                              20

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
ttcgttccga tgctctatga c                                            21

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
ccataaccta atttctctct c                                            21

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
gtcatgagac cctcaacaat                                              20

<210> SEQ ID NO 28
<211> LENGTH: 3085
<212> TYPE: DNA
<213> ORGANISM: Artificial Sequence
<220> FEATURE:
<223> OTHER INFORMATION: multiple replicon

<400> SEQUENCE: 28
ggtctcatgc cgttgttgtg actccgaggg gttgcctcaa actctatctt ataaccggcg    60
tggaggcatg gaggcagggg tattttggtc attttaatag atagtggaaa atgacgtgga   120
atttacttaa agacgaagtc tttgcgacaa ggggggggccc acgccgaatt taatattacc   180
ggcgtggccc ccccttatcg cgagtgcttt agcacgagcg gtccagattt aaagtagaaa   240
atttcccgcc cactagggtt aaaggtgttc acactataaa agcatatacg atgtgatggt   300
atttgatgga gcgtatattg tatcaggtat ttccgttgga tacgaattat tcgtacgacc   360
ctcgctttgg gtacgtcacg tggctcgagc gcgtagtcct cggtaatatc gcagaacaaa   420
agtacctgat atcgagtgta cttcaagtca gtgggaaatc aataaaatga ttatttttatg   480 aatatatttc attgtgcaag tagatagaaa ttacatatgt tacataacac acgaaataaa   540 caaaaaaga caatccaaaa acaaacaccc caaaaaaaat aatcacttta gataaactcg   600
tatgaggaga ggcacgtgat cgctagtgcc tgagacgcca gtgccttagg caggtgcgag   660
tacgctcgac acctgcggta gggatccacg tctcagggac tttgggtatc acgtggctcg   720
```

```
agcgcgtagt cctcggtaat atcgcagaac aaaagtacct gatatcgagt gtacttcaag    780
tcagtgggaa atcaataaaa tgattatttt atgaatatat ttcattgtgc aagtagatag    840
aaattacata tgttacataa cacacgaaat aaacaaaaaa agacaatcca aaaacaaaca    900
ccccaaaaaa aataatcact ttagataaac tcgtatgagg agaggcacgt tgccgggtag    960
cagaaggcat gttgttgtga ctccgagggg ttgcctcaaa ctctatctta taaccggcgt   1020
ggaggcatgg aggcaggggt attttggtca ttttaataga tagtgaaaaa tgacgtggaa   1080
tttacttaaa gacgaagtct tgcgacaag ggggggccca cgccgaattt aatattaccg    1140
gcgtggcccc cccttatcgc gagtgcttta gcacgagcgg tccagattta aagtagaaaa   1200
tttcccgccc actagggtta aaggtgttca cactataaaa gcatatacga tgtgatggta   1260
tttgatggag cgtatattgt atcaggtatt tccgttggat acgaattatt cgtacgaccc   1320
tcggcgcgtg ccttgtcttc gtcgactagt ctagaagaca agggaagctt tgggtacgtc   1380
acgtggctcg agcgcgtagt cctcggtaat atcgcagaac aaaagtacct gatatcgagt   1440
gtacttcaag tcagtgggaa atcaataaaa tgattatttt atgaatatat ttcattgtgc   1500
aagtagatag aaattacata tgttacataa cacacgaaat aaacaaaaaa agacaatcca   1560
aaaacaaaca ccccaaaaaa aataatcact ttagataaac tcgtatgagg agaggcacgt   1620
tgcctcagtg actcgacgat tcccgagcaa aaaagtctc cccgtcacac atgtagtggg    1680
tgacgcaatt atctttaaag taatccttct gttgacttgt cattgataac atccagtcct   1740
cgtcaggatt gcaaagaatt atagaaggga tcccacccttt tattttcttc ttttttccat   1800
atttagggtt gacagtgaaa tcagactggc aacctattaa ttgcttccac aatgggacga   1860
acttgaaggg gatgtcgtcg atgatattat aggtggcgtg ttcatcgtag ttggtgaaat   1920
cgatggtacc gttccaatag ttgtgtcgtc cgagacttct agcccaggtg gtctttccgg   1980
tacgagttgg tccgcagatg tagaggctgg ggtgtcggat tccattcctt ccattgtcct   2040
tgttaaatcg gccatccatt caaggtcaga ttgagcttgt tggtatgaga caggatgtat   2100
gtaagtataa gcgtctatgc ttacatggta tagatgggtt tccctccagg agtgtagatc   2160
ttcgtggcag cgaagatctg attctgtgaa gggcgacaca tacggttcag gttgtggagg   2220
gaataatttg ttggctgaat attccagcca ttgaagcttt gttgcccatt catgagggaa   2280
ttcttccttg atcatgtcaa gatattcctc cttagacgtt gcagtctgga taatagttct   2340
ccatcgtgcg tcagatttgc gaggagaaac cttatgatct cggaaatctc ctctggtttt   2400
aatatctccg tcctttgata tgtaatcaag gacttgttta gagtttctag ctggctggat   2460
attagggtga tttccttcaa aatcgaaaaa agaaggatcc ctaatacaag gttttttatc   2520
aagctggaga agagcatgat agtgggtagt gccatcttga tgaagctcag aagcaacacc   2580
aaggaagaaa ataagaaaag gtgtgagttt ctcccagaga aactggaata aatcatctct   2640
ttgagatgag cacttgggat aggtaaggaa aacatattta gattggagtc tgaagttctt   2700
actagcagaa ggcattttgg gagttgttgt gactccgagg ggttgcctca aactctatct   2760
tataaccggc gtggaggcat ggaggcaggg gtattttggt catttttaata gatagtggaa   2820 aatgacgtgg aatttactta aagacgaagt ctttgcgaca agggggggcc cacgccgaat   2880
ttaatattac cggcgtggcc ccccttatc gcgagtgctt tagcacgagc ggtccagatt    2940
taaagtagaa aatttcccgc ccactagggt taaaggtgtt cacactataa aagcatatac   3000
gatgtgatgg tatttgatgg agcgtatatt gtatcaggta tttccgttgg atacgaatta   3060
ttcgtacgac cctcgggatg agacc                                         3085
```

<210> SEQ ID NO 29
<211> LENGTH: 4196
<212> TYPE: DNA
<213> ORGANISM: Artificial Sequence
<220> FEATURE:
<223> OTHER INFORMATION: HDR template

<400> SEQUENCE: 29

```
ggaggagttt ggtccccaag tacttaaatt ggtccccaag tacttaccac aacacttgtc        60
ggtgagatta tttaatgctg attagattag acaaaaatta attagttttg agtagtggcg       120
taagtgtaaa taattagtct cttttttaac ttagaaaata gtttaatcct tagtataaat       180
agtcaaaatc actggaatga aaaacagttt ttaattttc caaatttgat tctgatacca        240
tgttaaattc gtggttcaaa atcactgcaa tgaaaagagc aatattgttt aacttttttt       300
aggaaaatcg aattgattta tagtcagttg atatagagtg aatacataag gaacatatac       360
agttgataca attgtataat tcgttcatac acttaataca aagtgaaccc acaaggaaca       420
tatacactta atataattgt attccttgat acaaaccaat tttgttcgtg tctctactct       480
ctatttcaat ttcgcttgac tctttacttt ttctaatatg tagctataaa tcgtaattaa       540
acaatactat atctctaaat ctcttattaa gctcaaacta tggtcatatt cgaaaaaatc       600
cttttaaata ttggtcccct ctcacgatta atgatagtta taactaacat tcaaatttta       660
gttgtacttg acatctaaaa cttaaaaaat agtacaagtt aactttttct ttttttaaa       720
aaaaggaaat acttgtattt attttttaa tatatagtta tattttggt tatttgaaaa         780
tacttgatct gtcatgtatg ctcagttaaa tatcgtcaca ttatagagaa aaaagtaata      840
ggagaaaaaa attaaaaatt atttcgaaaa atcaaaattt tttttgatt gaaatgaaag        900
atgggtttcc caatcgaggc tggcaggata ggtacattgg gaaatttgga tttgtgtgtt       960
gaaaatgatt gttcaattg gcttttataa catttgtcgt ttataaggtg tagaaggctc       1020
tctacaagtt ggtagttaca atttaataca cctgaattcg gatccggagc ggagaattaa      1080
gggagtcacg ttatgacccc cgccgatgac gcgggacaag ccgttttacg tttggaactg      1140
acagaaccgc aacgttgaag gagccactga gccgcgggtt tctggagttt aatgagctaa      1200
gcacatacgt cagaaaccat tattgcgcgt tcaaaagtcg cctaaggtca ctatcagcta      1260
gcaaatattt cttgtcaaaa atgctccact gacgttccat aaattcccct cggtatccaa      1320
ttagagtctc atattcactc tcctattttt acaacaatta ccaacaacaa caaacaacaa      1380
acaacattac aattacattt acaattacca tggttgaaca agatggattg cacgcaggtt      1440
ctccggccgc ttgggtggag aggctattcg gctatgactg ggcacaacag acaatcggct      1500
gctctgatgc cgccgtgttc cggctgtcag cgcaggggcg cccggttctt tttgtcaaga      1560
ccgacctgtc cggtgccctg aatgaactgc aggacgaggc agcgcggcta tcgtggctgg      1620
ccacgacggg cgttccttgc gcagctgtgc tcgacgttgt cactgaagcg ggaagggact      1680
ggctgctatt gggcgaagtg ccggggcagg atctcctgtc atctcacctt gctcctgccg      1740
agaaagtatc catcatggct gatgcaatgc ggcggctgca tacgcttgat ccggctacct      1800
gcccattcga ccaccaagcg aaacatcgca tcgagcgagc acgtactcgg atggaagccg      1860
gtcttgtcga tcaggatgat ctggacgaag agcatcaggg gctcgcgcca gccgaactgt      1920
tcgccaggct caaggcgcgc atgcccgacg gcgaggatct cgtcgtgact catggcgatg      1980
cctgcttgcc gaatatcatg gtggaaaatg gccgcttttc tggattcatc gactgtggcc      2040
```

```
ggctgggtgt ggcggaccgc tatcaggaca tagcgttggc tacccgtgat attgctgaag    2100
agcttggcgg cgaatgggct gaccgcttcc tcgtgcttta cggtatcgcc gctcccgatt    2160
cgcagcgcat cgccttctat cgccttcttg acgagttctt ctgagcggga ctctggggtt    2220
cgctagagtc ctgctttaat gagatatgcg agacgcctat gatcgcatga tatttgcttt    2280
caattctgtt gtgcacgttg taaaaaacct gagcatgtgt agctcagatc cttaccgccg    2340
gtttcggttc attctaatga atatatcacc cgttactatc gtatttttat gaataatatt    2400
ctccgttcaa tttactgatt gtaccctact acttatatgt acaatattaa aatgaaaaca    2460
atatattgtg ctgaataggt ttatagcgac atctatgata gagcgccaca ataacaaaca    2520
attgcgtttt attattacaa atccaattt aaaaaaagcg gcagaaccgg tcaaacctaa    2580
aagactgatt acataaatct tattcaaatt tcaaaagtgc cccaggggct agtatctacg    2640
acacaccgag cggcgaacta ataacgctca ctgaagggaa ctccggttcc ccgccggcgc    2700
gcatgggtga gattccttga agttgagtat tggccgtccg ctctaccgaa agttacgggc    2760
accattcaac ccgtccagc acggcggccg ggtaaccgac ttgctgcccc gagaattatg    2820
cagcattttt ttggtgtatg tgggcccaa atgaagtgca ggtcaaacct tgacagtgac    2880
gacaaatcgt tgggcgggtc cagggcgaat tttgcgacaa catgtcgagg ctcagccgct    2940
gtcagtcaac atggtggagc acgacactct ggtctactcc aaaaatgtca agatacagt    3000 ctcagaagat caaagggcta ttgagacttt tcaacaaagg ataatttcgg gaaacctcct    3060
cggattccat tgcccagcta tctgtcactt catcgaaagg acagtagaaa aggaaggtgg    3120
ctcctacaaa tgccatcatt gcgataaagg aaaggctatc attcaagatc tctctgccga    3180
cagtggtccc aaagatggac ccccacccac gaggagcatc gtggaaaaag aagaggttcc    3240
aaccacgtct acaaagcaag tggattgatg tgacatctcc actgacgtaa gggatgacgc    3300
acaatcacac tatccttcgc aagacccttc ctctatataa ggaagttcat tcatttgga    3360 gaggacacgc tcgagtataa gagctcattt ttacaacaat accaacaac acaaacaac    3420 aaacaacatt acaattacat ttacaattat cgatacaatg aagtatatat agacaataaa    3480
aaagtagtat aatatattat caaattatta tgaacagtac atctatgtcc tcattggag    3540 tgagaaaagg ttcatggact gatgaagaag attttcttct aagaaaatgt attgataagt    3600
atggtgaagg aaaatggcat cttgttccca taagagctgg taactattaa attaactatc    3660
acgttatttt tatttgtctt tctgtctcat tttatttgac gttattacga atatcatctg    3720
aaaatgtacg tgcaggtctg aatagatgtc ggaaaagttg tagattgagg tggctgaatt    3780
atctaaggcc acatatcaag agaggtgact ttgaacaaga tgaagtggat ctcattttga    3840
ggcttcataa gctcttaggc aacaggcatg caagtttatg ttttgacaaa atttgattag    3900
tatatattat atatacgtgt gactatttca tctaaatgtt acgttatttt acgtagatgg    3960
tcacttattg ctggtagact tcccggaagg acagctaacg atgtgaaaaa ctattggaac    4020
actaatcttc taaggaagtt aaatactact aaaattgttc ctcgcgaaaa gattaacaat    4080
aagtgtggag aaattagtac taagattgaa attataaaac ctcaacgacg caagtatttc    4140
tcaagcacaa tgaagaatgt tacaaacaat aatgtaattt tggacgagga ggaaca        4196
```

<210> SEQ ID NO 30
<211> LENGTH: 4302
<212> TYPE: DNA
<213> ORGANISM: Artificial Sequence
<220> FEATURE:
<223> OTHER INFORMATION: human codon optimized SpCas9

```
<400> SEQUENCE: 30
atgcccaaga agaagcgcaa ggtgggacgc gtctgcagga tatcaagctt gcggtaccgc    60
gggcccggga tcgccaccat ggataaaaag tattctattg gtttagacat cggcactaat   120
tccgttggat gggctgtcat aaccgatgaa tacaaagtac cttcaaagaa atttaaggtg   180
ttggggaaca cagaccgtca ttcgattaaa agaatcttac ggtgccct cctattcgat    240
agtggcgaaa cggcagaggc gactcgcctg aaacgaaccg ctcggagaag gtatacacgt   300
cgcaagaacc gaatatgtta cttacaagaa atttttagca atgagatggc caaagttgac   360
gattctttct ttcaccgttt ggaagagtcc ttccttgtcg aagaggacaa gaaacatgaa   420
cggcacccca tctttggaaa catagtagat gaggtggcat atcatgaaaa gtacccaacg   480
atttatcacc tcagaaaaaa gctagttgac tcaactgata agcggacct gaggttaatc    540
tacttggctc ttgcccatat gataaagttc cgtgggcact ttctcattga gggtgatcta   600
aatccggaca actcggatgt cgacaaactg ttcatccagt tagtacaaac ctataatcag   660
ttgtttgaag agaaccctat aaatgcaagt ggcgtggatg cgaaggctat tcttagcgcc   720
cgcctctcta atcccgacg gctagaaaac ctgatcgcac aattacccgg agagaagaaa    780
aatgggttgt tcggtaacct tatagcgctc tcactaggcc tgacaccaaa ttttaagtcg   840
aacttcgact tagctgaaga tgccaaattg cagcttagta aggacacgta cgatgacgat   900
ctcgacaatc tactggcaca aattggagat cagtatgcgg acttatttt ggctgccaaa    960
aaccttagcg atgcaatcct cctatctgac atactgagag ttaatactga gattaccaag  1020
gcgccgttat ccgcttcaat gatcaaaagg tacgatgaac atcaccaaga cttgacactt  1080
ctcaaggccc tagtccgtca gcaactgcct gagaaatata aggaaatatt ctttgatcag  1140
tcgaaaaacg ggtacgcagg ttatattgac ggcggagcga gtcaagagga attctacaag  1200
tttatcaaac ccatattaga gaagatggat gggacggaag agttgcttgt aaaactcaat  1260
cgcgaagatc tactgcgaaa gcagcggact ttcgacaacg gtagcattcc acatcaaatc  1320
cacttaggcg aattgcatgc tatacttaga aggcaggagg atttttatcc gttcctcaaa  1380
gacaatcgtg aaaagattga gaaaatccta acctttcgca taccttacta tgtgggaccc  1440
ctggcccgag ggaactctcg gttcgcatgg atgacaagaa agtccgaaga acgattact   1500
ccatggaatt tgaggaagt tgtcgataaa ggtgcgtcag ctcaatcgtt catcgagagg   1560
atgaccaact ttgacaagaa tttaccgaac gaaaaagtat tgcctaagca cagtttactt  1620
tacgagtatt tcacagtgta caatgaactc acgaaagtta agtatgtcac tgagggcatg  1680
cgtaaacccg cctttctaag cggagaacag aagaaagcaa tagtagatct gttattcaag  1740
accaaccgca aagtgacagt taagcaattg aaagaggact actttaagaa aattgaatgc  1800
ttcgattctg tcgagatctc cggggtagaa gatcgattta atgcgtcact tggtacgtat  1860
catgacctcc taaagataat taagataag gacttcctgg ataacgaaga gaatgaagat  1920
atcttagaag atatagtgtt gactcttacc ctctttgaag atcgggaaat gattgaggaa  1980
agactaaaaa catacgctca cctgttcgac gataaggtta tgaaacagtt aaagaggcgt  2040
cgctatacgg gctggggacg attgtcgcgg aaacttatca acgggataag agacaagcaa  2100
agtggtaaaa ctattctcga ttttctaaag agcgacggct tcgccaatag aaactttatg  2160
cagctgatcc atgatgactc tttaaccttc aaagaggata tacaaaaggc acaggtttcc  2220
ggacaagggg actcattgca cgaacatatt gcgaatcttg ctggttcgcc agccatcaaa  2280
```

| | |
|---|---|
| aagggcatac tccagacagt caaagtagtg gatgagctag ttaaggtcat gggacgtcac | 2340 |
| aaaccggaaa acattgtaat cgagatggca cgcgaaaatc aaacgactca gaagggggcaa | 2400 |
| aaaaacagtc gagagcggat gaagagaata gaagagggta ttaaagaact gggcagccag | 2460 |
| atcttaaagg agcatcctgt ggaaaatacc caattgcaga acgagaaact ttacctctat | 2520 |
| tacctacaaa atggaaggga catgtatgtt gatcaggaac tggacataaa ccgtttatct | 2580 |
| gattacgacg tcgatcacat tgtaccccaa tccttttga aggacgattc aatcgacaat | 2640 |
| aaagtgctta cacgctcgga taagaaccga gggaaaagtg acaatgttcc aagcgaggaa | 2700 |
| gtcgtaaaga aaatgaagaa ctattggcgg cagctcctaa atgcgaaact gataacgcaa | 2760 |
| agaaagttcg ataacttaac taaagctgag aggggtggct tgtctgaact tgacaaggcc | 2820 |
| ggatttatta acgtcagct cgtggaaacc cgccaaatca caagcatgt tgcacagata | 2880 |
| ctagattccc gaatgaatac gaaatacgac gagaacgata agctgattcg ggaagtcaaa | 2940 |
| gtaatcactt taaagtcaaa attggtgtcg gacttcagaa aggatttca attctataaa | 3000 |
| gttagggaga taaataacta ccaccatgcg cacgacgctt atcttaatgc cgtcgtaggg | 3060 |
| accgcactca ttaagaaata cccgaagcta gaaagtgagt ttgtgtatgg tgattacaaa | 3120 |
| gtttatgacg tccgtaagat gatcgcgaaa agcgaacagg agataggcaa ggctacagcc | 3180 |
| aaatacttct tttattctaa cattatgaat ttctttaaga cggaaatcac tctggcaaac | 3240 |
| ggagagatac gcaaacgacc tttaattgaa accaatgggg agacaggtga atcgtatgg | 3300 |
| gataagggcc gggacttcgc gacggtgaga aaagttttgt ccatgcccca agtcaacata | 3360 |
| gtaaagaaaa ctgaggtgca gaccggaggg ttttcaaagg aatcgattct tccaaaaagg | 3420 |
| aatagtgata agctcatcgc tcgtaaaaag gactgggacc cgaaaaagta cggtggcttc | 3480 |
| gatagcccta cagttgccta ttctgtccta gtagtggcaa aagttgagaa gggaaaatcc | 3540 |
| aagaaactga agtcagtcaa agaattattg gggataacga ttatggagcg ctcgtcttt | 3600 |
| gaaaagaacc ccatcgactt ccttgaggcg aaaggttaca aggaagtaaa aaaggatctc | 3660 |
| ataattaaac taccaaagta tagtctgttt gagttagaaa atggccgaaa acggatgttg | 3720 |
| gctagcgccg gagagcttca aaaggggaac gaactcgcac taccgtctaa atacgtgaat | 3780 |
| ttcctgtatt tagcgtccca ttacgagaag ttgaaaggtt cacctgaaga taacgaacag | 3840 |
| aagcaacttt tgttgagca gcacaaacat tatctcgacg aaatcataga gcaaatttcg | 3900 |
| gaattcagta agagagtcat cctagctgat gccaatctgg acaaagtatt aagcgcatac | 3960 |
| aacaagcaca gggataaacc catacgtgag caggcggaaa atattatcca tttgttact | 4020 |
| cttaccaacc tcggcgctcc agccgcattc aagtattttg acacaacgat agatcgcaaa | 4080 |
| cgatacactt ctaccaagga ggtgctagac gcgacactga ttcaccaatc catcacggga | 4140 |
| ttatatgaaa ctcggataga tttgtcacag cttgggggtg acgccatcc ctatgacgtg | 4200 |
| cccgattatg ccagcctggg cagcggctcc cccaagaaaa aacgcaaggt ggaagatcct | 4260 |
| aagaaaaagc ggaaagtgga cggcattggt agtgggagct aa | 4302 |

<210> SEQ ID NO 31
<211> LENGTH: 3882
<212> TYPE: DNA
<213> ORGANISM: Artificial Sequence
<220> FEATURE:
<223> OTHER INFORMATION: human codon optimized LbCpf1

<400> SEQUENCE: 31

```
atgcccaaga agaagcgcaa ggtgggacgc gtctgcagga tatcaagctt gcggtaccgc      60
gggcccggga tcgccaccat gagcaagctg gagaagtttta caaactgcta ctccctgtct    120
aagaccctga ggttcaaggc catccctgtg ggcaagaccc aggagaacat cgacaataag    180
cggctgctgg tggaggacga gaagagagcc gaggattata agggcgtgaa gaagctgctg    240
gatcgctact atctgtcttt tatcaacgac gtgctgcaca gcatcaagct gaagaatctg    300
aacaattaca tcagcctgtt ccggaagaaa accagaaccg agaaggagaa taaggagctg    360
gagaacctgg agatcaatct gcggaaggag atcgccaagg ccttcaaggg caacgagggc    420
tacaagtccc tgtttaagaa ggatatcatc gagacaatcc tgccagagtt cctggacgat    480
aaggacgaga tcgccctggt gaacagcttc aatggcttta ccacagcctt caccggcttc    540
tttgataaca gagagaatat gttttccgag gaggccaaga gcacatccat cgccttcagg    600
tgtatcaacg agaatctgac ccgctacatc tctaatatgg acatcttcga aggtggac    660
gccatctttg ataagcacga ggtgcaggag atcaaggaga agatcctgaa cagcgactat    720
gatgtggagg atttctttga gggcgagttc tttaactttg tgctgacaca ggagggcatc    780
gacgtgtata acgccatcat cggcggcttc gtgaccgaga gcggcgagaa gatcaagggc    840
ctgaacgagt acatcaacct gtataatcag aaaaccaagc agaagctgcc taagtttaag    900
ccactgtata agcaggtgct gagcgatcgg gagtctctga gcttctacgg cgagggctat    960
acatccgatg aggaggtgct ggaggtgttt agaaacaccc tgaacaagaa cagcgagatc   1020
ttcagctcca tcaagaagct ggagaagctg ttcaagaatt ttgacgagta ctctagcgcc   1080
ggcatctttg tgaagaacgg ccccgccatc agcacaatct ccaaggatat cttcggcgag   1140
tggaacgtga tccgggacaa gtggaatgcc gagtatgacg atatccacct gaagaagaag   1200
gccgtggtga ccgagaagta cgaggacgat cggagaaagt ccttcaagaa gatcggctcc   1260
ttttctctgg agcagctgca ggagtacgcc gacgccgatc tgtctgtggt ggagaagctg   1320
aaggagatca tcatccagaa ggtggatgag atctacaagg tgtatggctc ctctgagaag   1380
ctgttcgacg ccgattttgt gctggagaag agcctgaaga gaacgacgc cgtggtggcc   1440
atcatgaagg acctgctgga ttctgtgaag agcttcgaga attacatcaa ggccttcttt   1500
ggcgagggca aggagacaaa cagggacgag tccttctatg cgattttgt gctggcctac   1560
gacatcctgc tgaaggtgga ccacatctac gatgccatcc gcaattatgt gacccagaag   1620
ccctactcta aggataagtt caagctgtat tttcagaacc ctcagttcat gggcggctgg   1680
gacaaggata aggagacaga ctatcgggcc accatcctga gatacggctc caagtactat   1740
ctggccatca tggataagaa gtacgccaag tgcctgcaga gatcgacaa ggacgatgtg   1800
aacggcaatt acgagaagat caactataag ctgctgcccg ccctaataa gatgctgcca   1860
aaggtgttct tttctaagaa gtggatggcc tactataacc ccagcgagga catccagaag   1920
atctacaaga atggcacatt caagaagggc gatatgttta acctgaatga ctgtcacaag   1980
ctgatcgact ctttaagga tagcatctcc cggtatccaa agtggtccaa tgcctacgat   2040
ttcaactttt ctgagacaga gaagtataag gacatcgccg gcttttacag agaggtggag   2100
gagcagggct ataaggtgag cttcgagtct gccagcaaga aggaggtgga taagctggtg   2160
gaggagggca agctgtatat gttccagatc tataacaagg acttttccga taagtctcac   2220
ggcacaccca atctgcacac catgtacttc aagctgctgt ttgacgagaa caatcacgga   2280
```

```
cagatcaggc tgagcggagg agcagagctg ttcatgaggc gcgcctccct gaagaaggag    2340
gagctggtgg tgcacccagc caactcccct atcgccaaca agaatccaga taatcccaag    2400
aaaaccacaa ccctgtccta cgacgtgtat aaggataaga ggttttctga ggaccagtac    2460
gagctgcaca tcccaatcgc catcaataag tgccccaaga acatcttcaa gatcaataca    2520
gaggtgcgcg tgctgctgaa gcacgacgat aacccctatg tgatcggcat cgataggggc    2580
gagcgcaatc tgctgtatat cgtggtggtg gacggcaagg gcaacatcgt ggagcagtat    2640
tccctgaacg agatcatcaa caacttcaac ggcatcagga tcaagacaga ttaccactct    2700
ctgctggaca agaaggagaa ggagaggttc gaggcccgcc agaactggac ctccatcgag    2760
aatatcaagg agctgaaggc cggctatatc tctcaggtgg tgcacaagat ctgcgagctg    2820
gtggagaagt acgatgccgt gatcgccctg gaggacctga actctggctt taagaatagc    2880
cgcgtgaagg tggagaagca ggtgtatcag aagttcgaga agatgctgat cgataagctg    2940
aactacatgg tggacaagaa gtctaatcct tgtgcaacag gcggcgccct gaagggctat    3000
cagatcacca ataagttcga gagctttaag tccatgtcta cccagaacgg cttcatcttt    3060
tacatccctg cctggctgac atccaagatc gatccatcta ccggctttgt gaacctgctg    3120
aaaaccaagt ataccagcat cgccgattcc aagaagttca tcagctcctt tgacaggatc    3180
atgtacgtgc ccgaggagga tctgttcgag tttgccctgg actataagaa cttctctcgc    3240
acagacgccg attacatcaa gaagtggaag ctgtactcct acggcaaccg gatcagaatc    3300
ttccggaatc ctaagaagaa caacgtgttc gactgggagg aggtgtgcct gaccagcgcc    3360
tataaggagc tgttcaacaa gtacggcatc aattatcagc agggcgatat cagagccctg    3420
ctgtgcgagc agtccgacaa ggccttctac tctagcttta tggccctgat gagcctgatg    3480
ctgcagatgc ggaacagcat cacaggccgc accgacgtgg attttctgat cagccctgtg    3540
aagaactccg acggcatctt ctacgatagc cggaactatg aggcccagga gaatgccatc    3600
ctgccaaaga acgccgacgc caatggcgcc tataacatcg ccagaaaggt gctgtgggcc    3660
atcggccagt tcaagaaggc cgaggacgag aagctggata aggtgaagat cgccatctct    3720
aacaaggagt ggctggagta cgcccagacc agcgtgaagc acgcctatcc ctatgacgtg    3780
cccgattatg ccagcctggg cagcggctcc cccaagaaaa aacgcaaggt ggaagatcct    3840
aagaaaaagc ggaaagtgga cggcattggt agtgggagct aa                      3882
```

METHOD FOR INCREASING EFFICIENCY OF HOMOLOGOUS RECOMBINATION-BASED GENE EDITING IN PLANT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/000501, filed Jan. 11, 2019, which claims priority to the benefit of Korean Patent Application No. 10-2018-0007579 filed in the Korean Intellectual Property Office on Jan. 22, 2018, the entire contents of which are incorporated herein by reference.

TECHNICAL FIELD

The present invention relates to a method for increasing the efficiency of homologous recombination-based gene editing in a plant.

BACKGROUND ART

Developing a method for commercializing the gene editing technique by using homologous recombination (HR)-based or homology-directed DNA repair (HDR) in plant system is an area that is considered to be the holy grail of plant engineering. HR easily occurs in meiosis of germ line cells, yielding haploids, but it hardly occurs in mitosis of somatic cells. HDR is a repair pathway which occurs, along with non-homologous end joining (NHEJ), in case of having DNA damage. However, it is also reported that HDR occurs at a frequency of $\frac{1}{1,000}$ compared to NHEJ. It has been reported in the early 90s that an increased HDR can be caused by a double strand break (DSB) in tobacco plant (*Nicotiana* species), and the gene scissors or genome engineering/editing technique for DSB-induced modification of genome has been known since 20 years ago or so. However, use of the genome engineering/editing technique in plant system remains very restricted, and, in recent years, studies are actively made to increase the HRD efficiency by introducing the third-generation CRISPR/Cas9 system. When a DSB is created in a gene at specific site of a genome according to application of the CRISPR/Cas9 system, due to the incorrect repair occurring during DNA repair via NHEJ pathway, which is a predominant DNA repair pathway in somatic ells, various kinds of insertion-deletion (Indel) mutations are often generated. Although the technique is useful for obtaining random Indel mutations, it is not a genome engineering/editing technique in true sense. Technique for freely modifying a DNA sequence like target-specific insertion of foreign gene, deletion of a specific DNA fragment, replacement of specific DNA fragment with similar DNA, or the like are indeed a HDR-based genome engineering/editing technique. In this regard, the result showing that a significant increase in the HRD efficiency can be obtained by inducing DSB served as a very important basis of the HDR study. However, in spite of the fact that the HDR efficiency can be significantly increased by inducing DSB, the HDR efficiency remained at low level, i.e., about $\frac{1}{100}$ of NHEJ, so it seemed highly unlikely that the HDR can be applied in actual cases. As such, many efforts have been made to improve the DSB-based plant HDR technique, and, among them, the noticeable progress is obtained with use of a viral replicon.

Baltes et. al. (2014, Plant Cell 26 (1): 151-163) showed that, according to the amplification of HDR template by using ZFN (zinc finger nuclease) and geminivirus-based virus replicon previously known to be capable of inducing HDR, the HDR efficiency can be significantly increased in tobacco (*Nicotiana tabacum*). Specifically, the geminivirus-based virus replicon containing ZFN and HDR template was harbored in T-DNA, and, after the injection to tobacco using *Agrobacterium*, a circular replicon was yielded based on rolling circle replication, and expression of ZFN was allowed to occur. Subsequently, as a result of inducing DSB in defective GUS target gene, HDR occurs due to the HDR template harbored in the replicon. It is recently reported that this technique works well when TALENs (transcription activator-like effector nucleases) and Cas9 (CRISPR associated protein 9) are also used in tomato (Cermak et. al., 2015, Genome Biology 16 (1): 232). In the literature, the authors indicated that the HDR efficiency is about 10 to 13% per cotyledon based on the number of callus having anthocyanin over-accumulated by HDR. However, when converted in terms of the number of insertion invents of T-DNA in genome at the same conditions, the efficiency is 1 to 1.5%, and when converted in terms of the cells transiently expressing TALEN and Cas9, the efficiency is 0.1 to 0.15%, both remaining at still low level. When comparison is made with the T-DNA system in which conventional DSB is used only, it is considered that there is an increase of at least 5 to 10 times. However, as the estimation is made based on a callus having HDR events, an additional loss will occur for obtaining a plant with HDR so that it is expected to be at the level of about 1 target plant per 1,000 plants. In addition, since a reporter needs to be used due to the anthocyanin accumulation and characteristics like herbicide resistance or antibiotics resistance have to be utilized, the HDR-based genome engineering/editing technique is far from commercialization. According to the result of the most recently-reported study, the HDR knock-in efficiency based on $T_0$ transformant is increased up to 19.4% by using WDV (Wheat dwarf virus) replicon in rice. In this case, however, not only a callus having Cas9 already expressed therein is used but also the selection is made by using antibiotics after NPTII construct, which is an antibiotics-resistant gene, is inserted to the HDR template, and thus it is still far from the achievement of a new plant breeding technique allowing only the editing of a nucleotide sequence of target gene without having insertion of any foreign gene (Wang et. al. 2017, Mol Plant. 10 (7): 1007-1010). Accordingly, the optimization of a process for obtaining HDR plant from HDR callus as well as further enhancement of the efficiency of obtaining HDR callus remains as a very important task to achieve.

The improvement of gene editing technique appears to be faster in animal system than plant, and, in case of mammals like mouse and human, HDR occurs at higher efficiency compared to plant. This may be based on the characteristics of an animal system in which a large number of molecules can be delivered partially in oligonucleotide form to a cell. Among the plant systems that have been used until now to enhance the HDR efficiency in plant somatic cells, the plant system known to have the highest efficiency involves use of a virus replicon to provide HDR. However, to have additional enhancement of HDR efficiency, it is expected that various factors are expressed and controlled simultaneously. However, there is a problem that, when such factors are introduced to a replicon, a replicon with larger size is yielded to give a lower copy number and a unstable replicon is yielded. As such, it seems that efforts need to be made to overcome those problems.

A phenomenon in which the HDR efficiency is enhanced according to a treatment with various small chemical compound is also reported. Among those compounds, several chemical inhibitors inhibiting NHEJ pathway in competitive relationship with HDR are known. Specifically, it is reported that a treatment with SCR7 pyrazine (2,3-dihydro-6,7-diphenyl-2-thioxo-4 (1H)-pteridinone), which is known to inhibit ligase IV, can increase HDR by 2 to 19 times approximately. It is also reported that a treatment with RS-1 (RAD51-stimulatory compound 1), which is known to increase the activity of recombinase RAD51, can increase the HDR efficiency in mouse, but no report is made whether or not the treatment exhibits the working effect also in a plant system.

Most plant tissue culture is carried out at 22-25° C., but it is not known whether or not CRISPR/Cas9 functions well at those temperatures. Recently, it is reported that Cas9 activity is activated in *Arabidopsis* system at a temperature of 37° C. to yield increased frequency of Indel mutation (LeBlanc et. al., 2018, Plant J. 93 (2): 377-386). However, no report has been made for Cpf1 (CRISPR from *Prevotella* and *Francisella* 1) enzyme, and a use in plant HDR has never been described.

Increasing the HDR efficiency to a practically and industrially applicable level is a highly valuable project. Currently, the HDR efficiency at cellular level remains at very low level, and, when estimation is made for obtaining a plant with such cell, industrial use is currently not feasible unless antibiotics- or herbicide-resistance is utilized. Accordingly, it is highly desirable to establish a system which can dramatically increase the HDR efficiency in a plant.

Meanwhile, in Korean Patent Application Publication No. 2017-0081268, "Nucleic acid construct for genome editing" relating to a plant cell comprising a tobacco rattle virus (TRV) sequence and a nucleic acid sequence construct encoding a single guide RNA (sgRNA) which mediates sequence-specific breakage in a target sequence of a genome of interest, and a use thereof for gene editing is disclosed. However, the method of the present invention which is directed to increasing the efficiency of homologous recombination-based gene editing in a plant is not disclosed.

SUMMARY

The present invention is devised under the circumstances that are described above. Specifically, to significantly increase the efficiency of homologous recombination technique, which has been studied with a plant at experimental level with low efficiency, by combining CRISPR gene scissors system, plant tissue culture conditions, and HDR-based DNA repair mechanism with activators or inhibitors of various molecules that are related to the use of multiple replicon, optimum conditions for increasing the efficiency of homologous recombination in a tomato plant are determined, and the present invention is completed accordingly.

To solve the problems that are described in the above, the present invention provides a method for increasing efficiency of homologous recombination-based gene editing in gene editing of a plant using a gene scissors system including optimizing temperature and photoperiod conditions during tissue culture of plant cells, using a multiple replicon, or regulating the HDR pathway of NHEJ pathway.

It is believed that, by enabling a technique of free gene editing, the method according to the present invention can replace a conventional Indel-based or base editor-based CRISPR genome editing technique, and, as it allows very accurate introduction of alleles that are useful for crops and can be used as a technique for pyramiding genes, which are introduced during development of GM (genetically modified) crops, at a specific site of a specific chromosome, the method can be applied for a new plant breeding technique for various crops. Furthermore, it is also considered that the method can be applied for tagging of various proteins or in planta plant engineering in the field of basic sciences.

BRIEF DESCRIPTION OF THE DRAWINGS

FIG. 2 is a diagram illustrating the strategy of the present invention for increasing, from the low HDR efficiency of initial plant somatic cells, the HDR efficiency in which the strategy of increasing the HDR efficiency is based on breaking double strands, increasing the copy number of HDR template, enhancing the activity of transformation/CRISPR gene scissors or HDR pathway, blocking the NHEJ pathway, enhancing the activity by expressing the enzymes of HDR pathway, and use of a multiple replicon or the like.

FIG. 3 is a diagram summarizing the result of determining the culture conditions for increasing the HDR efficiency using a tomato. Seed germination: treatment at 25° C. for 3 to 4 days at dark conditions and 3 to 4 days at light conditions; precultivation: 25° C. at dark conditions for 1 day; main cultivation: 25° C. at dark conditions for 2 days; subsequent cultivation: after removing *Agrobacterium* by washing 2 times with timentin or cefotaxime and drying over sterile Whatman paper, cultivation for 5 days, in the same selection medium at 25-31° C., light/dark period conditions followed by subsequent cultivation with an interval of 10 to 12 days.

FIG. 4 shows an image of tomato plant overexpressing anthocyanin, which is obtained by HDR-based gene editing resulting from initial search. HR ex 6-light/-dark means cultivation of serial number (i.e., $6^{th}$) of the HR experiment under light or dark conditions for 10 days.

FIG. 10 shows a change in the HDR efficiency according to a treatment with NHEJ inhibitor (SCR7 pyrazine).

DETAILED DESCRIPTION

To achieve the above-described object of the present invention, the present invention provides a method for increasing efficiency of homologous recombination-based gene editing in gene editing of a plant using a gene scissors system, including optimizing temperature and photoperiod conditions during tissue culture of plant cells, using a multiple replicon, or regulating homology-directed DNA repair (HDR) pathway or non-homologous end joining (NHEJ) pathway.

According to the method of one embodiment of the present invention, a method for increasing the efficiency of homologous recombination-based gene editing in a plant, in which the method includes optimizing temperature and photoperiod conditions during tissue culture of plant cells, using a multiple replicon, and regulating the HDR pathway or NHEJ pathway by using a multiple replicon, is provided.

In the method according to one embodiment of the present invention, the optimized temperature conditions of the tissue culture may be cultivation at 29 to 33° C. for the first 4 to 6 days after cocultivation of plant tissues followed by cultivation at 26 to 30° C. for the next 4 to 6 days, and preferably cultivation at 31° C. for the first 5 days followed by cultivation at 28° C. for the next 5 days, but not limited thereto. The optimized photoperiod conditions of the tissue culture may be short day conditions consisting of a light period for 6 to 10 hours and a dark period of 14 to 18 hours, and preferably a light period for 8 hours and a dark period of 16 hours, but not limited thereto. The optimized photoperiod conditions may vary depending on a type of a plant.

In the method according to one embodiment of the present invention, the replicon is a geminivirus-based replicon, and the geminivirus-based replicon according to the present invention may be BeYDV (Bean Yellow Dwarf virus), but not limited thereto.

Figure 17:
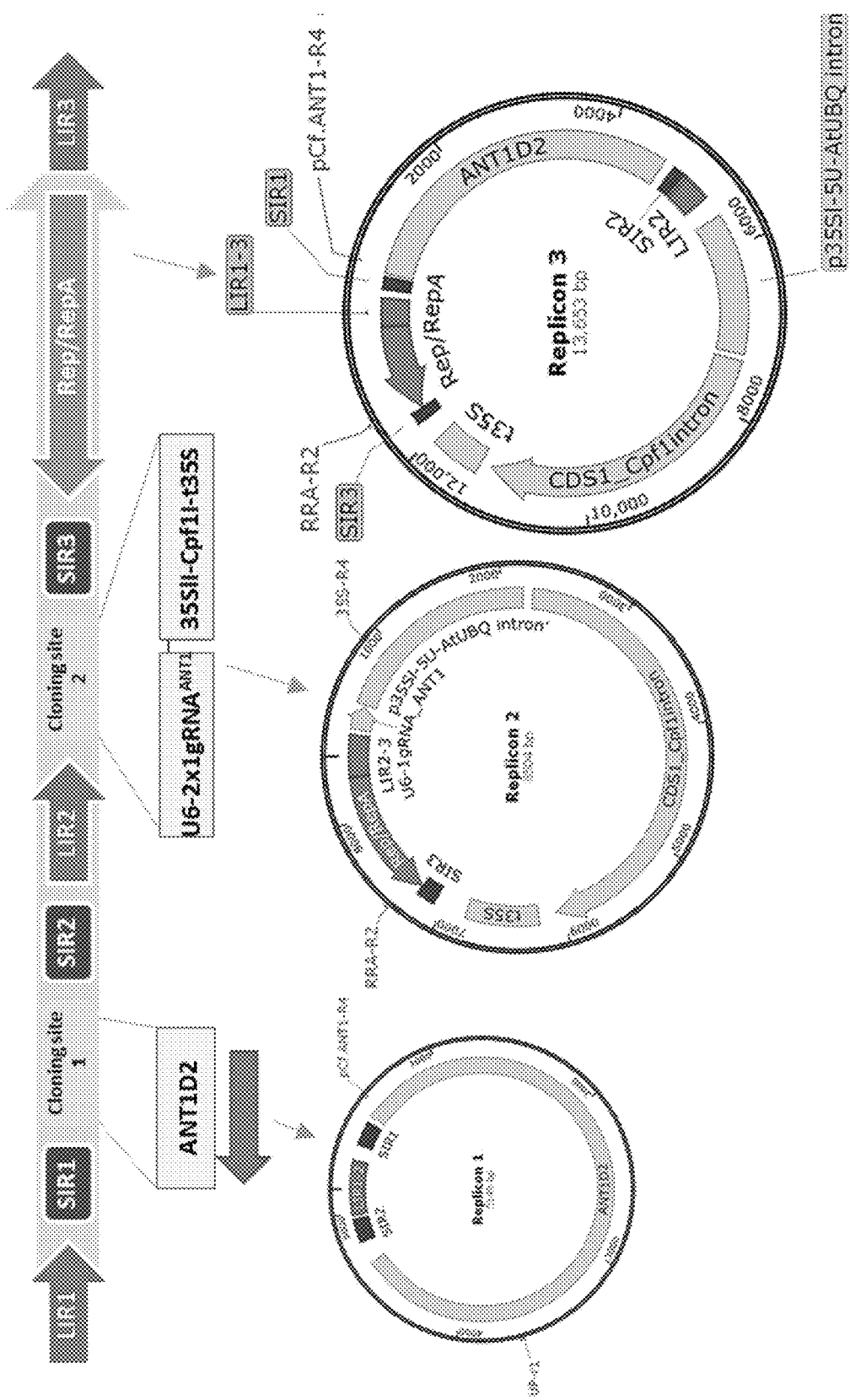
FIG. 17 shows the multiple replicon system and the replicon separated from the system. Three replicons are formed of three LIRs and three SIRs. Various HDR promoting factors in which the HDR template is formed of a single replicon to contain genomic DNA and Cpf1 expressing construct are expressed in other replicons.

The method according to one embodiment of the present invention is characterized in that, by constructing a multiple replicon system having HDR template, gRNA, and expression gene with three LIRs (large intergenic region) and three SIRs (small intergenic region), which are related to the regulation of HDR pathway, copy number of the HDR template is maximized and also various factors are expressed simultaneously at high level (FIG. 17). More specifically, the replicon according to the present invention may consist of the nucleotide sequence of SEQ ID NO. 28, but it is not limited thereto.

In the method according to one embodiment of the present invention, the regulation of HDR pathway may be activation of the HDR pathway by regulating the expression (i.e., induction or inhibition) of RPA1A (replication protein A), RPA1B, RPA1C, RPA1D, RAD51B (RAD51 paralog B), RAD51C, RAD51D, RAD51, DMC1 (DNA Meiotic Recombinase 1), RAD52-1, RAD52-2, RAD54, XRCC1 (X-Ray Repair Cross Complementing 1), XRCC2, XRCC3, ATM (ATM Serine/Threonine Kinase), XRS2/NBS (MRN/X), Mre11 (MRN/X), rad50 (MRN/X), Brca1 (BRCA1, DNA repair associated), Brca2A, Brca2B, CtIP/Com1/Sae2 or exo1, or activation of the HDR pathway by a treatment with an activator of the HDR pathway. The regulation of NHEJ pathway may be inhibition of the NHEJ pathway by inhibiting the expression of one or more selected from the group consisting of KU70 (XRCC6), KU80 (XRCC5) and LIG4 or by a treatment with an inhibitor therefor.

In the method according to one embodiment of the present invention, the gene scissors system may contain, as an effective component, one or more nuclease selected from the group consisting of Cas9 (CRISPR associated protein 9), Cpf1 (CRISPR from *Prevotella* and *Francisella* 1), TALEN (Transcription activator-like effector nuclease), ZFN (Zinc Finger Nuclease), and a functional homolog thereof, and a guide RNA capable of inducing the nuclease to a target genome site to be edited, but it is not limited thereto.

In the method according to one embodiment of the present invention, the nuclease is characterized in that AtTrp1 (*Arabidopsis thaliana* telomeric repeat-binding protein) intron consisting of the nucleotide sequence of SEQ ID NO. 1 is inserted to 3' of the coding sequence of the nuclease. More specifically, when the nuclease is SpCas9 (*Streptococcus pyogenes* Cas9), AtTrp1 intron sequence may be inserted to the 117 nt nucleotide position from the A of ATG of the coding sequence of SpCas9, and, when the nuclease is LbCpf1 (Lachnospiraceae bacterium ND2006 Cpf1), AtTrp1 intron sequence may be inserted to the 138 nt nucleotide position from the A of ATG of the coding sequence of LbCpf1.

The HDR efficiency currently achieved in a plant system is extremely low, and thus industrial use of HDR as a gene editing technique is inappropriate. Problems to be solved for increasing the HDR efficiency are as described below:
1) To achieve stable expression of nuclease like Cas9 and Cpf1 for effectively inducing DNA double strand break at a target gene site, since the double strand break is known to increase the HDR efficiency
2) To achieve stable replication of virus replicon, since HDR is dependent on copy number of HDR template
3) To optimize the transformation to have efficient delivery of the parts of gene scissors to inside of plant cells using *Agrobacterium*
4) To have high activity of Cas9 and Cpf1 when they are operating in a plant system
5) To achieve expression optimization based on cloning assembly optimization of several bioparts that are used for HDR.
6) To establish a genetic and chemical environment for achieving expression optimization of factors which participate in HDR.

To solve the problems that are described above, the present invention provides an optimization strategy and technique for each different stage.

I. HDR Effect According to DNA Double Stand Break

DNA double strand break is one of the critical elements for increasing the HDR efficiency. In the present invention, to have double strand break at a target site, human codon-optimized SpCas9 (SEQ ID NO. 30) or LbCpf1 (SEQ ID NO. 31) was used. By introducing AtTrp1 (*Arabidopsis thaliana* telomeric repeat-binding protein) intron (SEQ ID NO. 1) having an enhancer activity to CDS of SpCas9 and LbCpf1, stability of the gene expression and RNA to be expressed was achieved. Both SpCas9 and LbCpf1 CDS worked well for inducing tomato HDR, and the working efficiency thereof varied sensitively depending on a choice of the gRNA. According to one experiment in which LbCpf1 is used, two gRNAs having a separation distance of 50 nt or so exhibited better HDR effect than the double strand break using single gRNA. Furthermore, in order to achieve the stable expression of SpCas9 or LbCpf1, AtUBQ1 (*Arabidopsis thaliana* ubiquitin extension protein 1) number 1 intron (SEQ ID NO. 2) having an enhancer activity was added to the 5'UTR of 35S promoter, and stable expression was obtained accordingly.

II. Preparation of Replicon for Increasing HDR Efficiency

As HDR is dependent on copy number of HDR template, to have stable replication optimization of bean dwarf mosaic virus replicon, Kozak consensus sequence (SEQ ID NO. 3) was inserted in front of the initiation codon of Rep gene, and the translation efficiency of Rep was obtained accordingly.

III. Separate Preparation of Replicon-T-DNA for Increasing HDR Efficiency

Bean dwarf mosaic virus replicon was housed within T-DNA and introduced to plant cells by using *Agrobacterium*. It is known that, as the size of the replicon increases, the replicon would have inferior stability, transformability, or the like, and less copy number in plant cells. If the replicon size is excessively large as expression of various factors is required, it is possible to infect the same plant cells simultaneously by using two independent Agrobacteria, each containing different replicon T-DNA. However, as this method has poorer efficiency compared to the single *Agrobacterium* method, the inventors of the present invention used a multiple replicon system. According to transformation with single T-DNA having multiple replicon housed therein and separation into 2 or more replicons for working within cells, it can contribute to increasing the HDR efficiency. As the multiple replicon system of the present invention has 3 LIRs and 3 SIRs, it has a characteristic of being separated into 3 replicons at maximum when injected to cells (FIG. 17).

IV. Optimization of Culture Conditions for Plant Cells after Transformation Using *Agrobacterium*

Unlike animal cells, plants cells have a thick cell wall. As such, for the gene delivery using *Agrobacterium*, efficient delivery of parts of gene scissors to inside of plant cells using *Agrobacterium* is generally required, and also optimization of the forming and replication of a replicon from delivered T-DNA, expression of various tools of gene scissors, or the like is need.

To achieve those described in the above, the medium conditions for culturing plant cells like hormones for optimizing the transformation of plant cells using *Agrobacterium* have to be optimized. In addition, temperature and photoperiod (light treatment) conditions need to be optimized. In the present invention, temperature conditions of 19, 25, 28 and 31° C. were tested. As the temperature increases, the HDR efficiency has increased in all systems in which SpCas9 or LbCpf1 is used. However, at the higher concentrations, the long-time treatment increased the HDR events but the regeneration rate into a plant with an occurrence of HDR event was low. Thus, the optimum time was determined for 28° C. and 31° C. treatment, and, in the present invention, a 28° C./31° C. treatment for 5 days/5 days was selected. Furthermore, as a result of examining the HDR efficiency under dark conditions and dark/light period conditions like short-day treatment and long-day treatment, it was found that, in terms of the HDR efficiency, there is a no significant difference in SpCas9 systems at different photoperiod conditions. However, LbCpf1 system showed higher HDR efficiency from the photoperiod treatment compared to the dark period treatment. In addition, the short-day treatment exhibited higher HDR efficiency compared to the long-day treatment.

V. Necessity of Arrangement Optimization of Cassette Having Various Bioparts within Replicon In Order to Achieve the HDR with High Efficiency, it is Necessary to Optimize the expression through cloning assembly optimization of various bioparts that are used for HDR. Gene expression or copy number of the replicon may be affected by location, direction, or the like of a promoter or a terminator. In particular, a caution should be taken in examining the type of a promoter included in DNA, which is used as HDR template, so as to avoid forming of an RNA double strand.

VI. Genetic Optimization of HDR Pathway

For having genetic regulation of expression to achieve the optimized expression of factors which participate in HDR, genes of the HDR pathway present in tomato were examined first. According to the analysis of expression of the factors relating to the HDR pathway (RPA1A (replication protein A), RPA1B, RPA1C, RPA1D, RAD51B (RAD51 paralog B), RAD51C, RAD51D, RAD51, DMC1 (DNA Meiotic Recombinase 1), RAD52-1, RAD52-2, RAD54, XRCC1 (X-Ray Repair Cross Complementing 1), XRCC2, XRCC3, ATM (ATM Serine/Threonine Kinase), XRS2/NBS (MRN/X), Mre11 (MRN/X), rad50 (MRN/X), Brca1 (BRCA1, DNA repair associated), and Brca2A, Brca2B, CtIP/Com1/Sae2, exo1), SlMRE11, RAD51D, XRRC2, BRCA2, RAD54, ATM, RAD51, RAD52-1, and RAD51B genes were selected as a target gene. Then, one or two gRNA recognizing the promoter site were designed such that they can be expressed with use of a U6 promoter, and, at the same time, dCas9-sun tag//scAb-VP64 was expressed by using 35S promoter-5' UTR UBQ1 intron. In this case, dCas9-sun tag binds to the promoter via gRNA, and sun tag promotes the transcription via its binding to scAb (single chain Antibody)-VP64 activation effector. As an alternative mode, it is possible that a binding motif of pumilio protein or other RNA binding protein is linked to gRNA so that activation effector including VP64 can be directly collected by pumilio, or an amplification system of pumilio-sun tag//scAb-VP64 type can be used. In this case, the pumilio protein can be replaced with an RNA binding protein like MS2 (MS2 bacteriophage capsid RNA-binding protein) and dCsy4 (catalytically inactive Csy4), and VP64 can be also replaced with various activation effectors.

TABLE 1 gRNA of HDR pathway-related factors

|   |         | gRNA1HDR (SEQ ID NO.)              | Strand | gRNA2HDR                         | Strand |
|---|---------|------------------------------------|--------|----------------------------------|--------|
| 1 | S1MRE11 | ATCAAGTTAACGTTTATCTT (SEQ ID NO. 4) | m      | ATTAGAGATTATAAATTTAA (SEQ ID NO. 5) | m      |
| 2 | RAD51D  | tttacaataatatatagtaa (SEQ ID NO. 6) | p      | aagttgttagctagagtttc (SEQ ID NO. 7) | p      |
| 3 | XRRC2   | TTTTAAAAGAAAAAATTAAA (SEQ ID NO. 8) | m      | atacatatttatgtttgtta (SEQ ID NO. 9) | p      |
| 4 | BRCA2   | tgcccaactaacgctcaaaa (SEQ ID NO. 10) | p      | tgataataacaaaaatgacg (SEQ ID NO. 11) | p      |
| 5 | RAD54   | AAAAAAATTTGTATGTTGTT (SEQ ID NO. 12) | m      | tattattttatgttattga (SEQ ID NO. 13) | p      |
| 6 | ATM     | tagcatatgaccaaaataaa (SEQ ID NO. 14) | p      | taacaaaacagaaaaagaag (SEQ ID NO. 15) | p      |
| 7 | RAD51   | atgtgacccaatactttaag (SEQ ID NO. 16) | p      | tataccctta aactatattc (SEQ ID NO. 17) | p      |
| 8 | RAD52-1 | TTCTATGCATAAATAATTAA (SEQ ID NO. 18) | m      | gagagaaagaagcctcctca (SEQ ID NO. 19) | p      |
| 9 | RAD51B  | AGCTCTAAATGATAAAGTTG (SEQ ID NO. 20) | m      |                                  |        |

*m: minus strand; p: plus strand

VII. Chemical and Genetic Optimization of HDR Pathway

As a method which can be used either simultaneously or separately from the approaching method of above VI, there is a method of activating HDR pathway-regulating proteins by using chemical factors. In this regard, as a result of using RS-1 which works as an activators of RAD51, it was found that the HDR efficiency has increased by approximately 3 times.

VIII. HDR Optimization Via Genetic Regulation of Factors Inhibiting HDR or NHEJ Pathway in Competitive Relationship with HDR Pathway As a well-known protein of the NHEJ pathway, which is in competitive relationship with the HDR pathway, there are KU70 (XRCC6), KU80 (XRCC5), LIG4 and the like. In addition, various genes such as SMC6B, AtMMS21 (SMC5/6 component), ABO4, FAS1, RFC1, INO80, RecQ4a, FANCM, RecQ4b, RTEL1, or the like of which genetic mutation is known to promote HDR are present.

In the present invention, a method of increasing the HDR efficiency according to blocking of the NHEJ pathway by using Scr7 pyrazine chemical compound, which is an inhibitor of ligase IV of the NHEJ pathway in competitive relationship with the HDR pathway, was employed. As a result, when Scr7 pyrazine is used, the HDR efficiency had increased by 4 times compared to the comparative control group.

Hereinbelow, the present invention is explained in detail in view of the examples. However, the following examples are given only for exemplification of the present invention, and it is evident that the scope of the present invention is not limited by the examples.

Materials and Methods

1. Experimental Materials

The materials and reagents that are used in the present invention are as described in the following Table 2.

TABLE 2

Materials and reagents used in the present invention

| Plant materials | Source | Reagents | Source |
|---|---|---|---|
| Tomato variety Cultivar Hong-Kwang | Local company | Plant hormones; Acetosyringone; Hydrocarbon; β-D Glucuronide (X-Gluc); Chemicals for plant tissue culture; MS salts and vitamins; MS salts and B5 vitamins, | Sigma, USA; DUCHEFA Biochemie B.V., The Netherlands |
| Bacteria | | | |
| *Escherichia coli* 10-beta | NEB, USA | | |
| *Agrobacterium tumefaciens* GV3101::pMP90 | GNU. Korea | | |
| DNA vectors | | | |

TABLE 2-continued

Materials and reagents used in the present invention

| | Source | | Source |
|---|---|---|---|
| pTC147 | Addgene, | PhytoAgar, Maltose. | |
| pTC217 | USA | | |
| Golden Gate tool kit | | | |
| MoClo Tool kit | | | |
| Reagents | | | |
| dNTPs | Fermentas, Lithuania | H$_2$O | Treated with Millipore system (USA) |
| Phusion TaqDNA polymerase | | Kits | |
| PfuDNA polymerase | | RevertAid ™ H minus reverse transcriptase (1$^{st}$cDNAstrandsynthesis) | Fermentas, Lithuania |
| T4 DNA ligase | NEB, USA | FirstChoice ® RLM-RACE (5 RACE) | Invitrogene (Life Technology) |
| Restriction enzymes (BpiI, BsaI and others) | | CloneJE ™ PCR cloning | Fermentas, Lithuania |
| T7E1 endonuclease | | Plasmid DNA isolation kit (mini and midi); DNA extraction kit | BIOFACT, Korea; Qiagen, Germany |
| | | Total genomic DNA isolation kit (mini preps); Total RNA extraction kit | Qiagen, Germany |

2. DNA Amplification Using PCR

Composition of the PCR reactant and PCR amplification conditions used in the present invention are as described in the following Tables 3 and 4.

TABLE 3

Composition of PCR reactant

| Component | Concentration | Use amount (μl) |
|---|---|---|
| Reaction buffer | 10X | 2 |
| dNTPs | 2.5 mM | 2 |
| Forward primer | 10 μM | 1 |
| Reverse primer | 10 μM | 1 |
| Template DNA | 1-10 ng | 1 |
| Taq polymerase | 1 U/μl | 1 |
| Distilled water | — | up to 20 |

TABLE 4

Conditions of PCR reaction

| Step | Temperature (° C.) | Time | Number of cycle | |
|---|---|---|---|---|
| 1 | 94-95 | 4-5 min | 1 | Predenaturation |
| 2 | 94-95 | 20-60 seconds | 20-40 | Denaturation |
| 3 | primer Tm | 20-60 seconds | | Annealing |
| 4 | 72 | to 1 min/kb | | Extension |
| 5 | 72 | 1-10 min | 1 | Final extension |
| 6 | 4-15 | ∞ | — | Storage |

3. Agro-Infiltration

*Agrobacterium tumefaciens* GV3101::pMP90 strain was transformed with each HDR vector. *Agrobacterium*-mediated transient expression in tomato leaves was carried out by a pressure infiltration method. The *Agrobacterium* culture was cultured until the absorbance at 600 nm reaches 1.0, and, one hour before the infiltration, the culture was subjected to a treatment with 20004 acetosyringone.

4. Tomato Transformation and Virus Infection

Cotyledon explants of a tomato derived from Hong-Kwang variety, which has been cultivated in vitro conditions, were transformed by using *Agrobacterium* containing the HDR construct. Sterile seeds of Hong-Kwang variety were cultured in ½ MS medium (pH 5.8) containing 30 g/l sucrose at a temperature condition of 25±2° C. under light conditions for 16 hours/and dark conditions for 8 hours. The 7-day old shoots were collected and the cotyledons were finely chopped to a size of 0.2 to 0.3 cm. The finely-chopped pieces (i.e., explants) were placed in a plate containing the precultivation medium (MS basal salts, Gamborg B5 vitamins, 2.0 mg/l of Zeatin trans-isomer, 0.1 mg/l of indolyl acetic acid (IAA), 1 mM of putrescine, 30 g/l of glucose, pH 5.8) to have a pre-treatment for 1 day. The precultivated explants were poked with a sharp subject, and then transformed with *Agrobacterium tumefaciens* GV3101::pMP90 which contains the HDR construct. After that, the explants were transferred to a cocultivation medium and cultivated for 2 days at 25° C. under dark conditions. Then, the explants were transferred to a non-selective medium and cultivated for 5 days followed by subculture using a selective medium. The subculture was carried out with an interval of 10 days to obtain the maximum regeneration efficiency. When the stem has grown to a sufficient level (i.e., 1.5 to 3.0 cm), transfer to a rooting medium was made to have a fully grown plant. The plant grown from the rooting medium was acclimated by transfer to a vermiculite pot, and then transferred again to soil of a greenhouse which is maintained at temperature conditions of 26±2° C. and photoperiod of light for 16 hours/dark for 8 hours.

5. PCR-Based Detection of Release of BeYDV Replicon

To analyze the kinetic tendency of release of BeYDV circular replicon, single-constitution single-constitution BeYDV vector pLSL.GFP.R, pLSL.R.GGFP and non-viral vector pAGM4723 were used.

TABLE 5

Main vectors used in the present invention

| Construct name | Application |
|---|---|
| pLSL.GFP.R (Cermak et. al. 2015) | Virus Circularization detection |
| pLSL.R.GGFP | Virus Circularization detection |
| pAGM4723 | Non-viral vector, replicon detection control |
| pTC147 (Cermak et. al. 2015) | 35S:ANT1 expressing, non-replicating T-DNA transformation efficiency control |
| pTC217 (Cermak et. al. 2015) | BeYDV ANT1-GT T-DNA vector with Cas9/gRNA1b in the replicon |

Tomato cotyledon was transformed with *Agrobacterium* containing each vector described above. On day 2, day 5, day 9, day 12, day 16, and day 30 after the transformation, two cotyledons were collected from each group, washed with 400 mg/l timentin, and stored at −80° C. After that, genomic DNA was extracted from each sample by using CTAB (cetyl trimethyl ammonium bromide) method, and PCR was carried out using primers of the following Table 6. PCR product was loaded on a 1% (w/v) agarose gel, and band intensity was calculated by using Image J program (imagej.nih.gov/ij/) and standardized using GAPDH (glyceraldehyde 3-phosphate dehydrogenase).

TABLE 6

Primers for investigating replicon forming

| Primer | Sequence information (5'→3') (SEQ ID NO.) | Product size | Application |
|---|---|---|---|
| GR-F1 | TTGAGATGAGCACTTGGGATAG (SEQ ID NO. 21) | 545 bp | virus circularization detection in pLSL.GFP.R |
| 35S-R5 | CGTAAGCCTCTCTAACCATCTG (SEQ ID NO. 22) | | |
| GR-F1 | TTGAGATGAGCACTTGGGATAG (SEQ ID NO. 21) | 537 bp | virus circularization detection in pLSL.R.GGFP |
| tOCS-R1 | GTTCTGTCAGTTCCAAACGTAAA (SEQ ID NO. 23) | | |
| pVS1-F1 | ATCTCGCGGTACATCCAATC (SEQ ID NO. 24) | 521 bp | To detect vector Backbone from *Agrobacterium* in tomato |
| pVS1-R1 | TTCGTTCCGATGCTCTATGAC (SEQ ID NO. 25) | | |
| GADPH-F | CCATAACCTAATTTCTCTCTC (SEQ ID NO. 26) | 1208 bp | internal control |
| GADPH-R | GTCATGAGACCCTCAACAAT (SEQ ID NO. 27) | | |

6. Measurement of HDR Frequency

In order to measure the HDR frequency of Cas9, 21 days after the *Agrobacterium* infection, purple spots were counted from the cotyledon which has been infected with pTC217 (BeYDV with Cas9/gRNA1b) virus replicon and also from the cotyledon which has been transformed with pTC147 (35S:ANT1 T-DNA) control vector. By dividing the total number of purple spots that has been counted from callus generated with pTC217 by the total number of purple spots that has been counted from callus generated with pTC147, the HDR frequency rate was estimated.

Example 1. Analysis of Homologous Recombination Efficiency Using Anthocyanin Marker To examine the efficiency of HDR-based gene scissors in tomato, to the upstream promoter site of the transcription initiation site of ANT1 gene, which is a transcription factor regulating the anthocyanin synthesis, 35S promoter was inserted via HDR so that forming of purple-colored callus was induced based on anthocyanin overexpression resulting from the activation of ANT1 gene.

HDR template (SEQ ID NO. 29) was designed such that 35S promoter nucleotide sequence and pNos-NPTII-OCSt are inserted, at the upstream of the promoter, to have kanamycin resistance at the time of HDR event. In this case, the upper nucleotide sequence was 1,043 bp and the lower nucleotide sequence was 592 bp, in which the both nucleotides have sequence homology. In addition, two TALEN binding sites or dSaCas9 (D10A, N580A)/gRNA sites were added to the upstream region. For DNA double strand break, SpCas9 (*Streptococcus pyogenes* Cas9)/gRNA, LbCpf1 (Lachnospiraceae bacterium ND2006 Cpf1)/gRNA1, LbCpf1/gRNA1/gRNA2, or the like was used, and the design was made such that, in the HDR template, gRNA (guide RNA) complementary base sequence does not undergo any breakage with Cas9 or Cpf1, in accordance with site-specific mutation. Gene scissors replicon in the simplest form consists of SpCas9/LbCpf1, 1 or 2 gRNA, and ANT1 HR template, and dCas9 (dead Cas9)-based transcription activation system and dCas9-based HDR template accumulation system were additionally constituted. When HDR has occurred successfully, purple color was shown from the callus or plant due to the overaccumulation of anthocyanin. The HDR efficiency obtained until now was HDR event efficiency of about 20%, which is a divided value based on 35S-ANT1 vector, and one HDR plant was successfully obtained from 30 or so cotyledons.

Furthermore, in order to increase the HR efficiency, temperature and light conditions were modified in many different ways.

TABLE 7

Determination of initial temperature and light conditions for increasing HDR efficiency using tomato Hong-Kwang $F_1$

| No | Construct | HDR ex3 25° C. | HDR ex3 32° C. | HDR ex5 (30 dpt, light, 28° C.) | HDR ex5 (30 dpt, dark, 28° C.) |
|---|---|---|---|---|---|
| 1 | pTC147 | 289/29* | 282/32 | 413/54 | 411/52 |
| 2 | pTC217 | 5/31 | 13/33 | 10/69 | 28/60 |

*Number of purple callus/cotyledon number pTC147 indicates the number of callus per cotyledon, in which anthocyanin is formed in the callus as a result of T-DNA transformation, and pTC217 indicates the number of callus by HDR per cotyledon.

TABLE 8

Determination of HDR efficiency at other temperature conditions (results on Day 21 after cultivation)

| No | Temperature (° C.) | Construct | Total explant* | TPS[1] | HRE[2] | HRC[3] |
|---|---|---|---|---|---|---|
| 1 | 19 | pTC147 | 111 | 2164 | | |
|   |    | pTC217 | 157 | 19 | 11.97 ± 6.39 | 0.54 ± 0.25 |
| 2 | 25 | pTC147 | 131 | 2008 | | |
|   |    | pTC217 | 149 | 30 | 22.08 ± 8.86 | 1.57 ± 0.71 |
| 3 | 28 | pTC147 | 113 | 1714 | | |
|   |    | pTC217 | 150 | 60 | 47.62 ± 31.40 | 2.72 ± 1.59 |
| 4 | 31 | pTC147 | 116 | 1428 | | |
|   |    | pTC217 | 141 | 57 | 44.85 ± 15.54 | 3.84 ± 1.10 |

[*Test was repeated 4 times at the same conditions, TPS; total number of purple spots, HRE; average HDR efficiency (%) relative to total explants, HRC; average HDR efficiency standardized against total number of purple spots in pTC147 as control]

As shown in Table 8 above, higher HDR efficiency is obtained as the treatment is carried out at higher temperatures. Furthermore, the high standard deviations are believed to be caused by a confusion with the real gene editing, which results from the production of anthocyanin in immature tomato stem 21 days after the transformation.

Furthermore, analysis was made on the HDR efficiency for a case in which CRISPR/Cpf1 system or its upgrade system have been used. As a result, it was found that the HDR event was successfully shown from the initial construct version in which CRISPR/Cpf1 system has been used. 7711-1 and 7721-1 are both a control which does not contain Rep and gRNA, respectively (Table 9). Furthermore, with CRISPR/Cpf1 upgrade version, as the directionality was optimized at the time of preparing goldengate assembly level 2 to minimize the RNAi effect which results from the construct itself of the initial version, an improved effect was obtained compared to CRISPR/Cpf1-based construct of the existing initial version, and also more enhanced HR effect than CRISPR/Cas9-based construct, which has been suggested by other research groups, was shown (Table 10).

TABLE 9

Measurement of HDR efficiency using CRISPR/Cpf1 system

| No | Construct | Total explant | TPS | HRE | HRC |
|---|---|---|---|---|---|
| 1 | 7711-1 | 320 | 1 | 0.48 ± 0.48 | 0.03 ± 0.03 |
| 2 | 7721-1 | 233 | 1 | 0.46 ± 0.46 | 0.03 ± 0.03 |
| 3 | 7731-1 | 315 | 58 | 17.67 ± 7.86 | 1.01 ± 0.44 |

TABLE 10

Measurement of HDR efficiency using CRISPR/Cpf1 upgrade system

| No. | Construct | Temperature phase* | Total explant | TPS | HRE | HRC |
|---|---|---|---|---|---|---|
| 1 | pTC147 | 5.31-5.25 | 63 | 1073 | | |
|   |        | 5.31-5.28 | 63 | 1154 | | |
|   |        | 10.31 | 65 | 1084 | | |
| 2 | pTC217 | 5.31-5.25 | 43 | 23 | 53.46 ± 1.09 | 3.58 ± 0.74 |
|   |        | 5.31-5.28 | 69 | 37 | 54.80 ± 6.19 | 3.16 ± 0.64 |
|   |        | 10.31 | 70 | 47 | 67.80 ± 14.29 | 3.92 ± 0.75 |
| 3 | 8161-1 | 5.31-5.25 | 71 | 58 | 76.12 ± 18.96 | 4.51 ± 0.74 |
|   |        | 5.31-5.28 | 68 | 52 | 77.55 ± 5.84 | 4.43 ± 0.64 |
|   |        | 10.31 | 59 | 45 | 75.40 ± 3.97 | 4.44 ± 0.75 |
| 4 | 7731-1 | 5.31-5.25 | 70 | 28 | 40.78 ± 3.21 | 2.62 ± 0.55 |
|   |        | 5.31-5.28 | 75 | 25 | 32.25 ± 2.71 | 1.82 ± 0.27 |
|   |        | 10.31 | 75 | 22 | 29.32 ± 4.80 | 1.68 ± 0.09 |

TABLE 10-continued

Measurement of HDR efficiency using CRISPR/Cpf1 upgrade system

| No. | Construct | Temperature phase* | Total explant | TPS | HRE | HRC |
|---|---|---|---|---|---|---|
| 5 | 82611-2 | 5.31-5.25 | 24 | 1 | 4.17 | 0.34 |
|   |         | 5.31-5.28 | 28 | 3 | 10.71 | 0.67 |
|   |         | 10.31     | 23 | 1 | 4.35 | 0.26 |
| 6 | 8131-4  | 5.31-5.25 | 67 | 14 | 21.03 ± 6.22 | 1.35 ± 0.44 |
|   |         | 5.31-5.28 | 76 | 11 | 14.27 ± 6.40 | 0.81 ± 0.41 |
|   |         | 10.31     | 52 | 7 | 12.97 ± 12.97 | 0.77 ± 0.77 |
| 7 | 8141-2  | 5.31-5.25 | 66 | 6 | 10.50 ± 4.76 | 0.76 ± 0.45 |
|   |         | 5.31-5.28 | 73 | 4 | 6.35 ± 2.72 | 0.37 ± 0.18 |
|   |         | 10.31     | 77 | 4 | 4.53 ± 2.27 | 0.27 ± 0.14 |
| 8 | 8151-1  | 5.31-5.25 | 68 | 10 | 14.0 ± 5.60 | 0.81 ± 0.25 |
|   |         | 5.31-5.28 | 66 | 5 | 8.99 ± 4.50 | 0.48 ± 0.25 |
|   |         | 10.31     | 68 | 3 | 3.33 ± 3.33 | 0.16 ± 0.16 |

[*5.31-5.25, after cocultivation, explants were treated for 5 days at 31° C., and then treated for 5 days at 25° C.; 5.31-5.28, after cocultivation, explants were treated for 5 days at 31° C., and then treated for 5 days at 28° C.; 10.31, after cocultivation, explants were treated for 10 days at 31° C.]

Furthermore, the result of analyzing the HDR efficiency using CRISPR/Cpf1 upgrade version depending on photoperiod after the transformation is described in the following Table 11. It was found as shown in the following table that, in case of CRISPR/Cpf1-based construct, the efficiency has increased by almost 2 times at L/D conditions, in particular short day conditions, compared to DD conditions.

TABLE 11

Comparison of HDR efficiency depending on photoperiod employed after transformation

| No. | Construct | Photoperiod | Total explant | TPS | HRE | HRC |
|---|---|---|---|---|---|---|
| 1 | pTC147 | DD | 55 | 1147 | | |
|   |        | 8L/16D | 56 | 1116 | | |
|   |        | 16L/8D | 62 | 1260 | | |
| 2 | pTC217 | DD | 33 | 20 | 60.61 | 2.90 |
|   |        | 8L/16D | 41 | 32 | 78.05 | 3.61 |
|   |        | 16L/8D | 34 | 20 | 58.82 | 2.68 |
| 3 | 8161-1 | DD | 57 | 54 | 102.78 ± 30.56 | 4.94 ± 1.49 |
|   |        | 8L/16D | 59 | 124 | 206.82 ± 11.59 | 9.44 ± 0.66 |
|   |        | 16L/8D | 58 | 100 | 171.88 ± 3.88 | 7.91 ± 0.10 |
| 4 | 8253-2 | DD | 52 | 33 | 57.42 ± 39.25 | 2.75 ± 1.87 |
|   |        | 8L/16D | 73 | 46 | 58.84 ± 33.84 | 2.70 ± 1.58 |
|   |        | 16L/8D | 63 | 10 | 14.30 ± 4.30 | 0.66 ± 0.19 |
| 5 | 82611-2 | DD | 23 | 7 | 30.43 | 1.47 |
|   |         | 8L/16D | 12 | 5 | 41.67 | 1.87 |
|   |         | 16L/8D | 22 | 3 | 13.64 | 0.63 |

[DD: after cocultivation, explants were treated for 10 days at 31° C., dark conditions;

8L/16D: after cocultivation, explants were treated for 10 days at 31° C. with light period for 8 hours/dark period for 16 hours;

16L/8D: after cocultivation, explants were cultivated for 10 days at 31° C. with light period for 16 hours/dark period for 8 hours]

Example 2. Increased Plant Homologous Recombination Frequency According to SCR7 Pyrazine Treatment DNA repair is mostly achieved by NHEJ pathway, and HDR-based repair occurs very limitedly. According to previous studies made on mammals, it was reported that HDR efficiency can be increased by blocking the NHEJ pathway. It is reported that SCR7 pyrazine, which is an inhibitor of mammalian ligase IV, can increase HDR as much as about 19 times in mouse, or 5 times in human cell line. With regard to a plant, Nishizawa-Yokoi et. al. suggested that ligase IV plays an important role in NHEJ pathway in rice (2016, Plant Physiol. 170 (2): 653-666). However, no report has been made regarding the influence of SCR7 pyrazine on plant HDR. Accordingly, the effect of a treatment with different cultivation period (0, 1, 2 or 3 days) or different SCR7 pyrazine concentration (0, 1, 10 μM) was examined by the inventors of the present invention by using Cas9 structure pTC217 (BeYDV having Cas9/gRNA1b). As a result, it was found that the HDR frequency increases in accordance with an increase in the treatment time (period) and concentration of SCR7 pyrazine (Table 12 to Table 14).

TABLE 12

Change in HDR efficiency depending on treatment with NHEJ inhibitor (tomato cv. Tom-Heart, 21 dpi)

| Construct | | | | pTC147 (T-DNA) | | pTC217 | | |
| --- | --- | --- | --- | --- | --- | --- | --- | --- |
| NHEJ inhibitor-SCR7 (2nd treatment) concentration | Conditions | Temperature | Number of total cotyledons | Purple spot/ cotyledon (Avg.) | Purple spots (Total) | Purple spot/ cotyledon (Avg.) | Purple spots (Total) | Editing efficiency* |
| 0 | 16L/8D | 25° C. | 52 | 27.1 | 1409 | 0.88 | 46 | 3.2 |
| 1 μM | 16L/8D | 25° C. | 52 | 22.2 | 1154 | 1 | 52 | 4.5 |
| 10 μM | 16L/8D | 25° C. | 52 | 21.8 | 1137 | 2.61 | 136 | 11.9 |

[Editing efficiency: total purple spots (pTC217)/total purple spots (pTC147)×100]

TABLE 13

Change 1 in HDR efficiency depending on treatment period with NHEJ inhibitor (tomato cv. Hong-Kwang, 21 dpi)

| Construct | | | | | pTC147 (T-DNA) | | pTC217 | | |
| --- | --- | --- | --- | --- | --- | --- | --- | --- | --- |
| SCR7 treatment concentration | SCR7 treatment period | Photoperiod conditions* | Temperature | Number of total cotyledons | Purple spot/ cotyledon (Avg.) | Purple spots (Total) | Purple spot/ cotyledon (Avg.) | Purple spots (Total) | Editing efficiency* |
| 0 | | DD→16L/8D | 28° C. | 35 | 23.9 | 839 | 0.32 | 11 | 1.31 |
| 1 μM | 1 day | DD→16L/8D | 28° C. | 35 | 28.7 | 1005 | 0.55 | 19 | 1.89 |
| | 2 days | DD→16L/8D | 28° C. | 35 | 26.9 | 942 | 0.93 | 32 | 3.39 |
| | 3 days | DD→16L/8D | 28° C. | 35 | 23.2 | 813 | 1.8 | 63 | 7.74 |
| 10 μM | 1 day | DD→16L/8D | 28° C. | 35 | 20.1 | 703 | 0.68 | 24 | 3.41 |
| | 2 days | DD→16L/8D | 28° C. | 35 | 18.8 | 658 | 1.75 | 61 | 9.27 |
| | 3 days | DD→16L/8D | 28° C. | 35 | 14.2 | 497 | 3.26 | 114 | 22.93 |

[Photoperiod conditions: after dark treatment (DD) for 10 days, light treatment for 16 hours/dark treatment for 8 hours]

TABLE 14

Change 2 in HDR efficiency depending on treatment period with NHEJ inhibitor (tomato cv. Hong-Kwang, 21 dpi)

| Construct | | | | | pTC147 (T-DNA) | | pTC217 | | |
| --- | --- | --- | --- | --- | --- | --- | --- | --- | --- |
| SCR7 treatment concentration | SCR7 treatment period | Photoperiod conditions* | Temperature | Number of total cotyledons | Purple spot/ cotyledon (Avg.) | Purple spots (Total) | Purple spot/ cotyledon (Avg.) | Purple spots (Total) | Editing efficiency* |
| 0 | | DD→16L/8D | 28° C. | 35 | 20.9 | 732 | 0.90 | 31 | 4.23 |
| 1 μM | 1 day | DD→16L/8D | 28° C. | 35 | 26.0 | 912 | 1.96 | 68 | 7.45 |
| | 2 days | DD→16L/8D | 28° C. | 35 | 17.9 | 627 | 1.29 | 45 | 7.17 |
| | 3 days | DD→16L/8D | 28° C. | 35 | 18.9 | 663 | 1.44 | 50 | 7.54 |
| 10 μM | 1 day | DD→16L/8D | 28° C. | 35 | 22.9 | 802 | 2.60 | 91 | 11.34 |
| | 2 days | DD→16L/8D | 28° C. | 35 | 21.5 | 754 | 2.91 | 102 | 13.52 |
| | 3 days | DD→16L/8D | 28° C. | 35 | 18.8 | 660 | 2.85 | 100 | 15.15 |

Example 3. Kinetic Pattern of Release of BeYDV Replication Replicon

Figure 1:
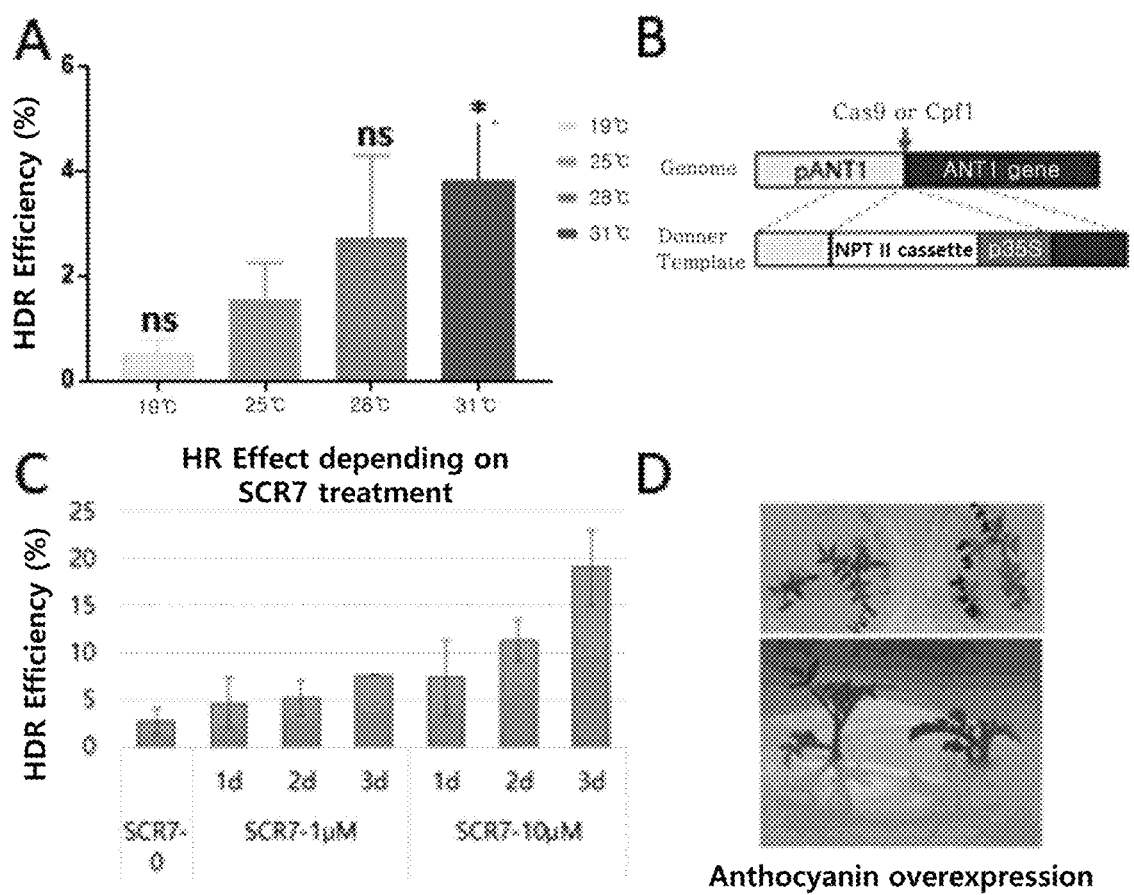
FIG. 1 illustrates (A) result showing the HDR efficiency depending on various temperature conditions of a treatment, (B) diagram of the reporter construct used for measurement of the HDR efficiency, (C) result showing that the efficiency of HDR-based gene editing has increased in accordance with a treatment with SCR7 pyrazine, which inhibits the NHEJ pathway, and (D) image of tomato plant which overexpresses anthocyanin due to HDR.
Figure 2:
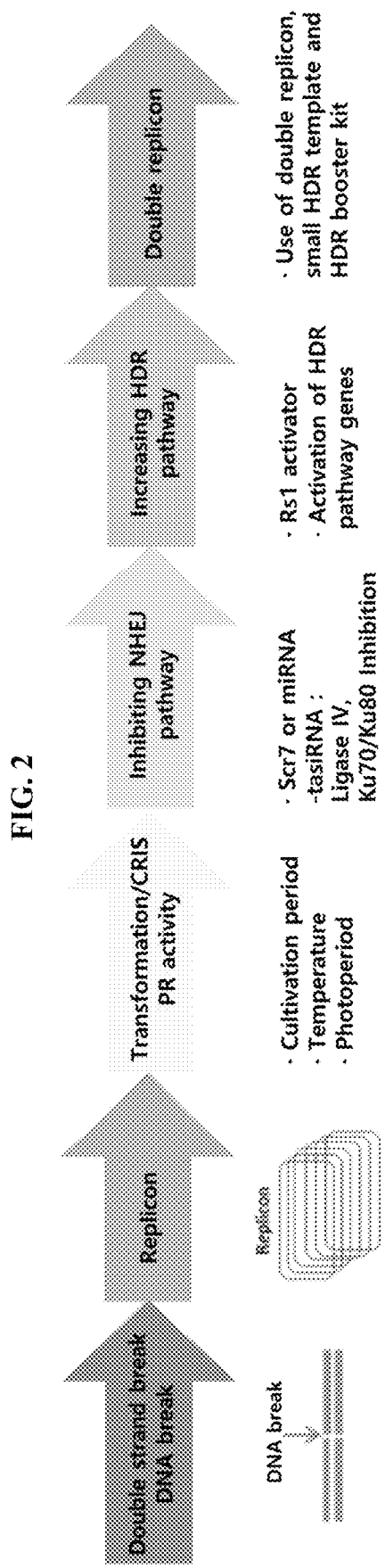
Figure 5:
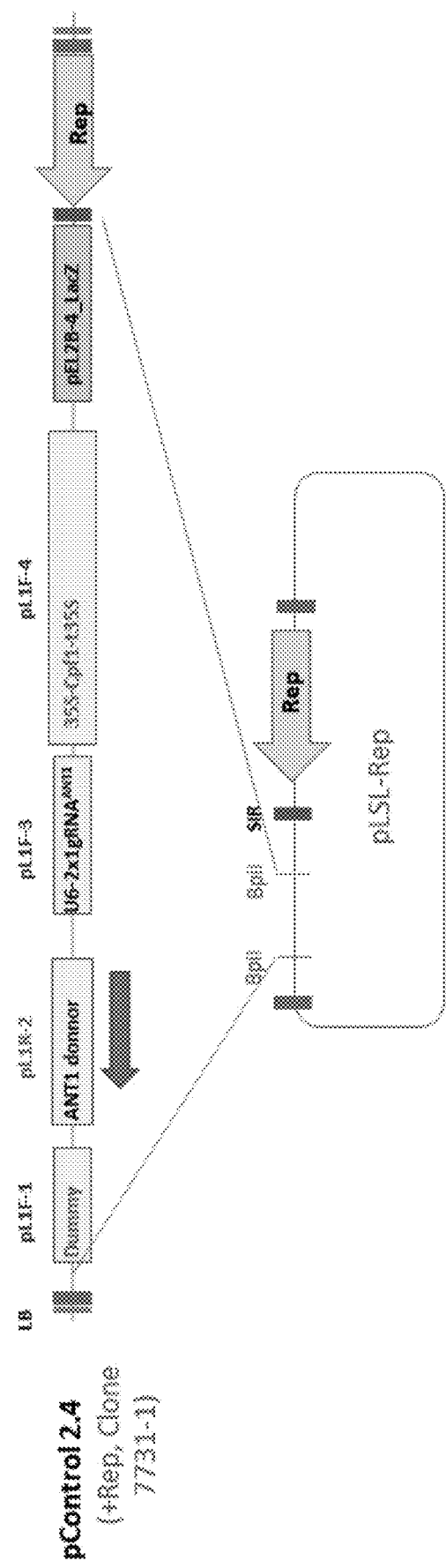
FIG. 5 illustrates the simplest structure of CRISPR/Cpf1-based HDR construct.
Figure 6:
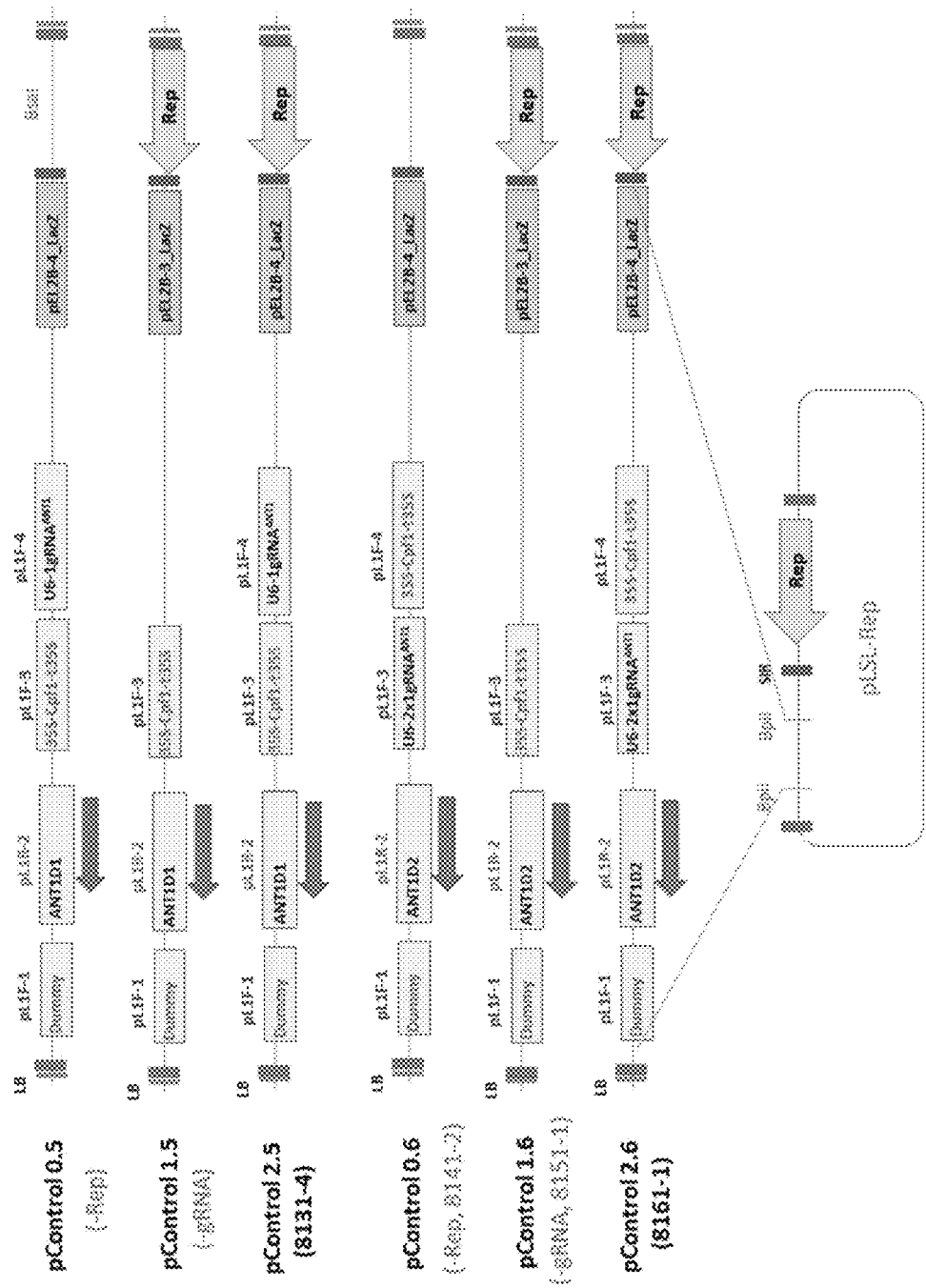
FIG. 6 shows dCRISPR/Cpf1-based HDR upgrade construct and control construct.
Figure 7:
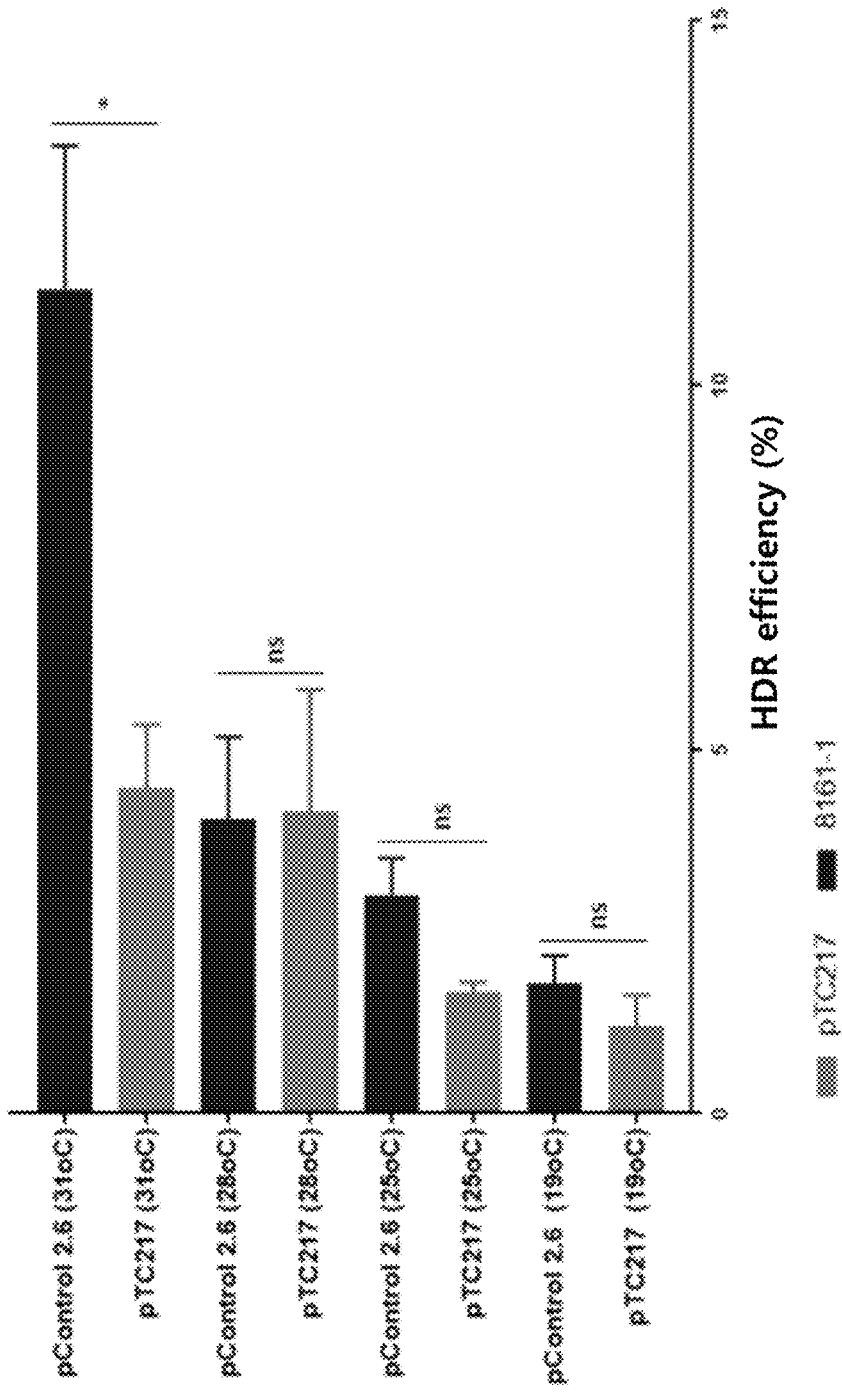
FIG. 7 shows a result exhibiting the HDR efficiency per cell with CRISPR construct at different temperature conditions. In the figure, *: p<0.05, ns: no significantly different.
Figure 8:
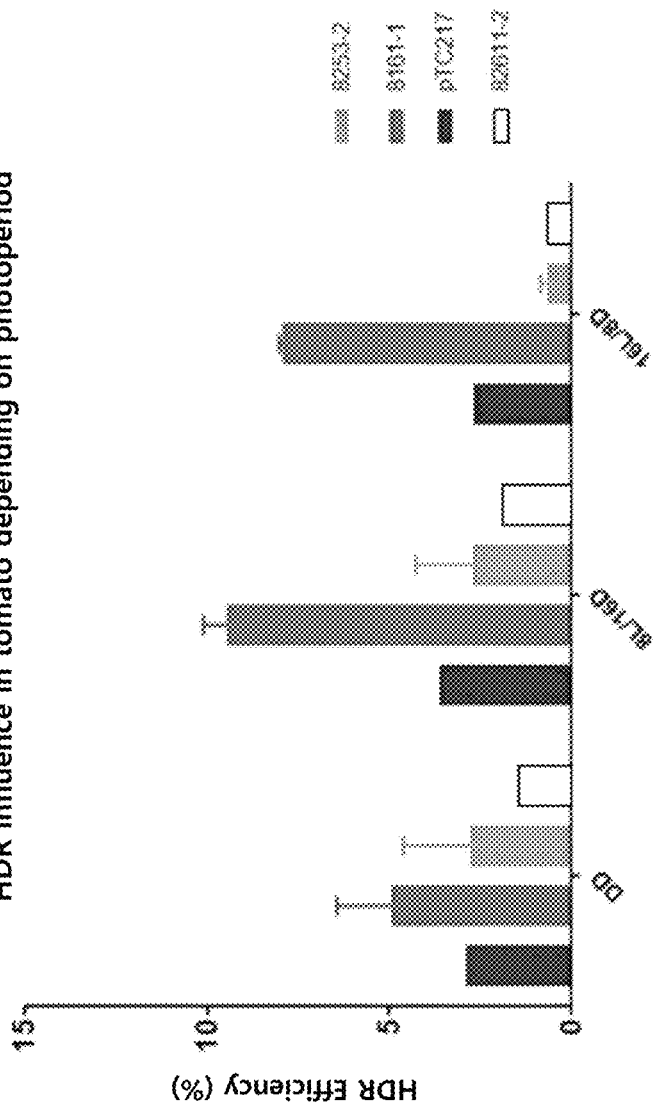
FIG. 8 shows the result exhibiting the HDR efficiency per cell with CRISPR construct under different photoperiod.
Figure 9:
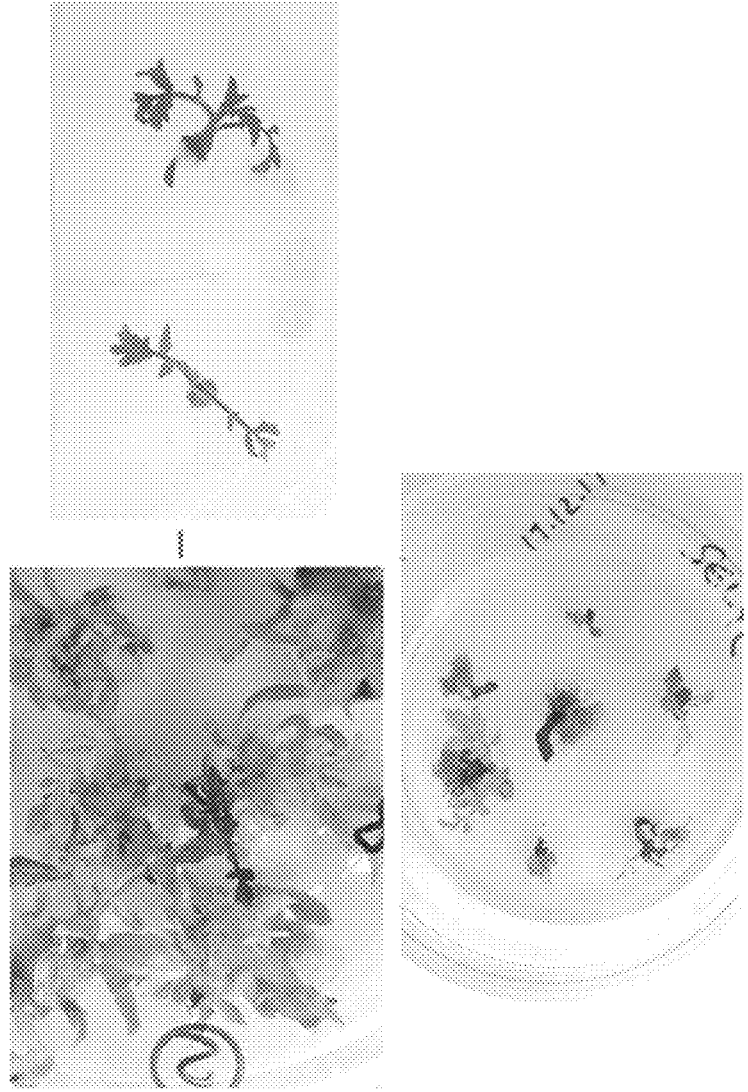
FIG. 9 shows an image of a plant with HDR event in which CRISPR/Cpf1-based construct has been used.
Figure 11:
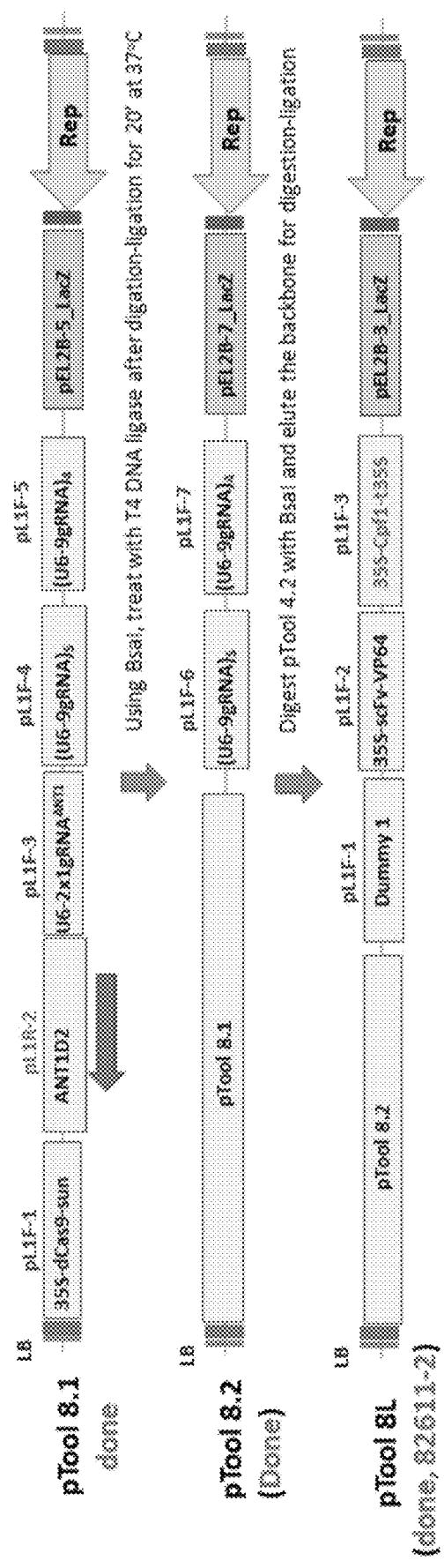
FIG. 11 shows CRISPR/Cpf1 and dCas9-sun constructs which can induce overexpression of a HDR pathway factor.
Figure 12:
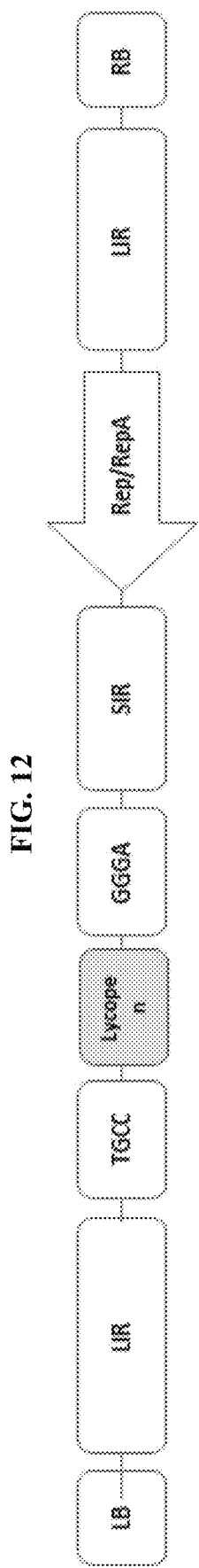
FIG. 12 is a diagram illustrating the structure of BeYDV-derived replicon.
Figure 13:
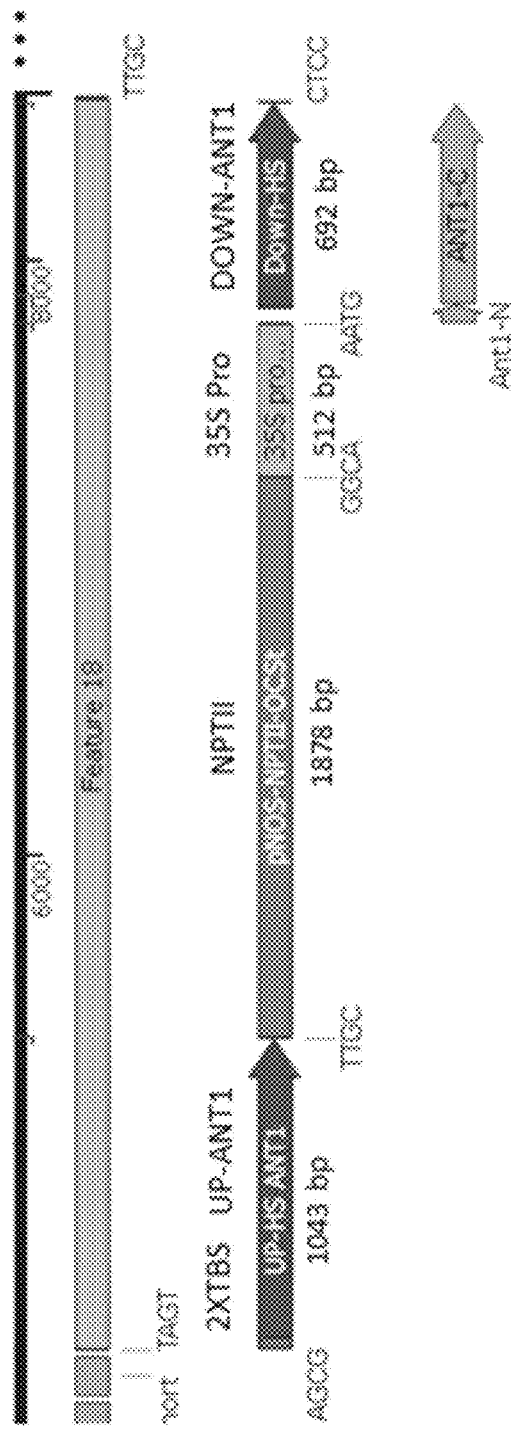
FIG. 13 shows the DNA constitution within ANT1 HDR template.
Figure 14:
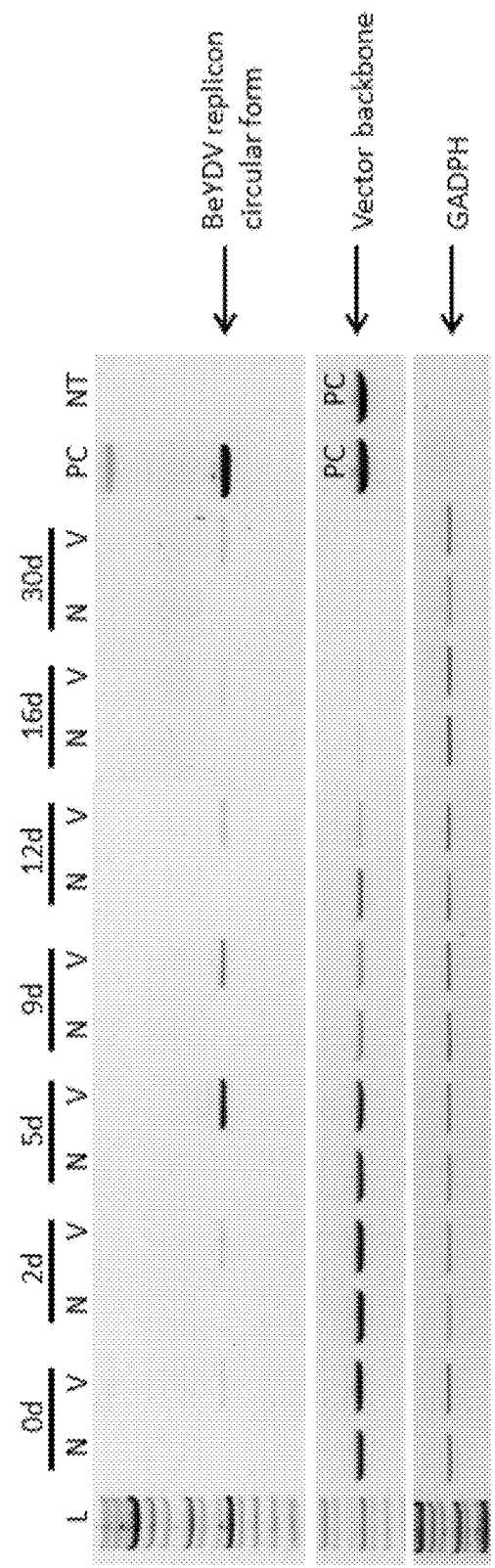
FIG. 14 shows the result of PCR analysis for determining the release of each virus vector in the genomic DNA which has been separated after different cultivation period from the cotyledon transformed with *Agrobacterium* containing BeYDV vector pLSL.R.GGFP, in which the analysis was made by using a specific primer for amplifying the junction part of LIR region.
Figure 15:
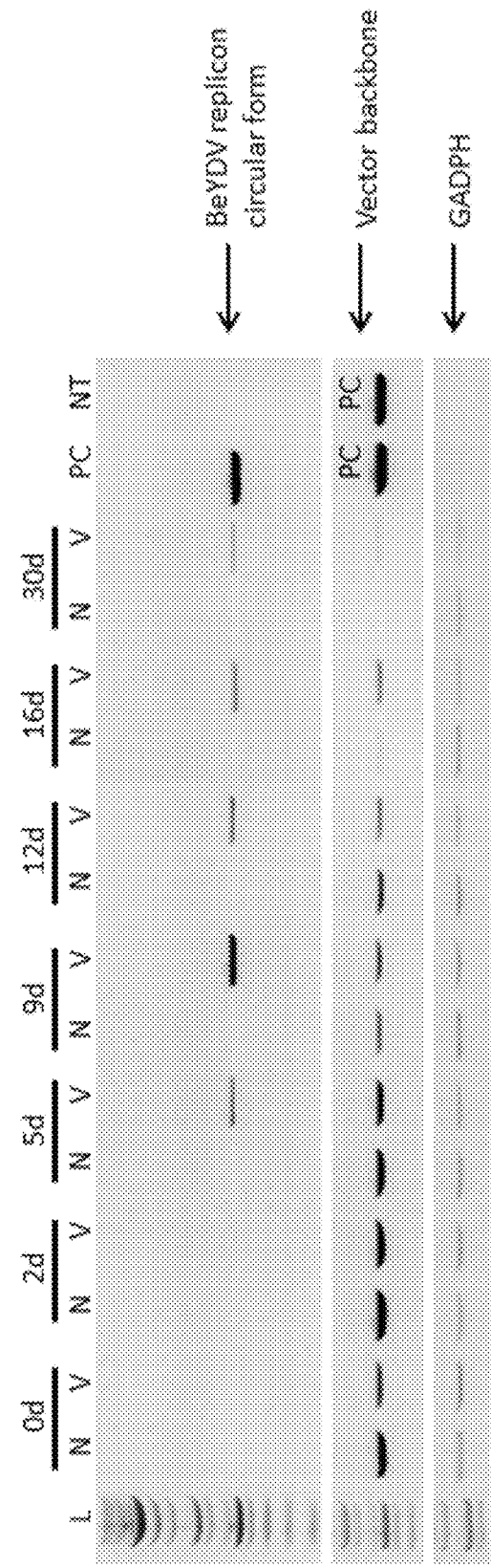
FIG. 15 shows the result of PCR analysis for determining the release of each virus vector in the genomic DNA which has been separated after different cultivation period from the cotyledon transformed with *Agrobacterium* containing BeYDV vector pLSL.GFP.R, in which the analysis was made by using a specific primer for amplifying the junction part of LIR region.
Figure 16:
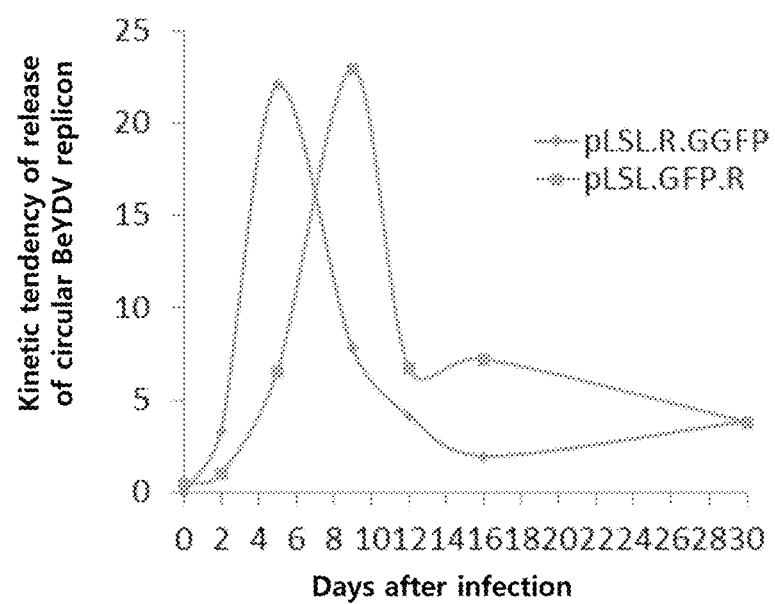
FIG. 16 shows the result of the kinetic analysis of the release pattern of virus copies of BeYDV vector pLSL.R.GGFP and pLSL.GFP.R.

The inventors of the present invention found the optimum time point of the maximum release of circular BeYDV replicon in *Agrobacterium*-infected tomato cotyledon system. Virus replicon tends to get expressed in circular form from a liner T-DNA which is delivered to a nucleus of plant cell, and, according to rolling circle replication, it is amplified to several hundred to several thousand copies per cell. Kinetic information about the maximum replicon release may provide information regarding the optimum time point for applying small molecules to a tissue culture system. To study the kinetic pattern of replicon release, cotyledon was transfected with *Agrobacterium* containing BeYDV vector pLSL.GFP.R (Cermak et. al., 2015) and pLSL.R.GGFP and non-virus vector pAGM4723. Circular virus was detected from the infected cotyledon, in which the detection is made by PCR analysis using specific primers which can amplify the junction part of two LIR regions in the separated genomic DNA. Stable presence of BeYDV replicon for 2 weeks to 8 weeks was reported previously for pLSL.GFP.R which contains *Agrobacterium*-infected tomato cotyledon. However, the maximum time of the release of virus copies has not been reported. By using samples of Day 2 to Day 30, the inventors of the present invention found from each analysis point that pLSL.GFP.R and pLSL.R.GGFP in BeLSV circular form are stably present. Two days after the infection, the circular replicon was at very low level in the vector system, but, after 5 days, it has suddenly increased to the maximum level in pLSL.R.GGFP vector system. In pLSL.GFP.R vector system, the maximum value gradually started to increase 9 days after the infection, while the replicon has decreased slowly but was maintained at stable level in the analysis sample during 30 days after the infection. No replicon was found from the non-virus vector sample (FIG. 14 to FIG. 16).

A sequence listing electronically submitted with the present application on Jul. 22, 2020 as an ASCII text file named 20200722_Q35620GR09_TU_SEQ, created on Jul. 20, 2020 and having a size of 26,000 bytes, is incorporated herein by reference in its entirety.

What is claimed is:

1. A method for increasing efficiency of homologous recombination-based gene editing in gene editing of a plant, the method comprising:
    transforming a plant cell with a vector comprising:
    a coding sequence of at least one nuclease selected from the group consisting of Cas9 (CRISPR associated protein 9), Cpf1 (CRISPR from *Prevotella* and *Franciselia* 1), TALEN (Transcription activator-like effector nuclease), ZFN (Zinc Finger Nuclease) and a functional homolog thereof;
    a coding sequence of a guide RNA capable of inducing the at least one nuclease to a target genome site to be edited; and a geminivirus-based multiple replicon; and
    tissue-culturing the transformed plant cell,
    wherein the tissue-culturing comprises a first cultivation at 31 to 33° C. for the first 4 to 6 days, followed her a second cultivation at 26 to 30° C. for the next 4 to 6 days.

2. The method of claim 1, wherein the tissue-culturing comprises short day conditions consisting of a light period for 6 to 10 hours and a dark period of 14 to 18 hours.

3. The method of claim 1, wherein the geminivirus-based multiple replicon has three large intergenic regions (LIRs) and three small intergenic regions (SIRs).

4. The method of claim 1, further comprising: activating homology-directed DNA repair (HDR) pathway by regulating expression of one or more selected from the group consisting of RPA1A (replication protein A), RPA1B, RPA1C, RPA1D, RAD51B (RAD51 paralog B), RAD51C, RAD51D, RAD51, DMC1 (DNA Meiotic Recombinase 1), RAD52-1, RAD52-2, RAD54, XRCC1 (X-Ray Repair Cross Complementing 1), XRCC2, XRCC3, ATM (ATM Serine/Threonine Kinase), XRS2/NBS (MRN/X), Mre1 1 (MRN/X), rad50 (MRN/X), Brca1 (BRCA1, DNA repair associated), Brca2A, Brca2B, CtIP/Com1/Sae2 or exo1, or by a treatment with an activator of the HDR pathway.

5. The method of claim 1, further comprising: inhibiting a non-homologous end joining (NHEJ) pathway by regulating expression of one or more selected from the group consisting of KU70 (XRCC6), KU80 (XRCC5) and LIG4 or by a treatment with an inhibitor of the NHEJ pathway.

6. The method of claim 1, wherein AtTrp1 (*Arabidopsis thaliana* telomeric repeat-binding protein) intron consisting of the nucleotide sequence of SEQ ID NO. 1 is inserted in coding sequence of the at least one nuclease.

* * * * *